US006824771B1

(12) United States Patent
Curiel et al.

(10) Patent No.: US 6,824,771 B1
(45) Date of Patent: Nov. 30, 2004

(54) INFECTIVITY-ENHANCED CONDITIONALLY-REPLICATIVE ADENOVIRUS AND USES THEREOF

(75) Inventors: David T. Curiel, Birmingham, AL (US); Victor Krasnykh, Birmingham, AL (US); Ramon Alemany, Birmingham, AL (US); Igor Dmitriev, Homewood, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/569,789

(22) Filed: May 12, 2000

Related U.S. Application Data

(60) Provisional application No. 60/133,634, filed on May 12, 1999.

(51) Int. Cl.[7] .................. A61K 35/76; A61K 48/00; C12N 15/861
(52) U.S. Cl. .................. 424/93.2; 435/320.1; 435/455; 435/456; 514/44
(58) Field of Search .................. 424/93.2; 514/44; 435/320.1, 325, 455, 456, 235; 530/350; 536/23.1

(56) References Cited

U.S. PATENT DOCUMENTS

| 5,801,029 A | * | 9/1998 | McCormick | ............. | 435/172.3 |
| 5,846,782 A | * | 12/1998 | Wickham et al. | ........... | 435/679 |
| 6,096,718 A | * | 8/2000 | Weitzman et al. | ............ | 514/44 |

FOREIGN PATENT DOCUMENTS

| WO | WO-96/17053 | * | 6/1996 |
| WO | WO-96/34969 | * | 11/1996 |

OTHER PUBLICATIONS

Eck et al., "Gene–based therapy." Goodman & Gilman's The Pharmacological Basis of Therapeutics—Ninth Edition, McGraw–Hill: 77–101, 1996.*
Bischoff et al., "An adenovirus mutant that replicates selectively in p53–deficient human tumor cells." Science, vol. 274: 373–376, Oct. 1996.*
Dachs et al., "Targeting gene therapy to cancer: A Review." Oncology Res., vol. 9: 313–325, 1997.*
Sandhu et al., "Human Gene Therapy." Critical Reviews in Biotechnol., vol. 17(4): 307–326, 1997.*
Roelvink et al., "The coxsackievirus–adenovirus receptor protein can function as a cellular attachment protein for adenovirus serotypes from subgroups A, C, D, E and F." J. Virol., vol. 72 (10): 7909–7915, 1998.
Dmitriev et al., "An adenovirus vector with genetically modified fibers demonstrates expanded tropism via utilization of a coxsackievirus and adenovirus receptor–independent cell entry mechanism." J. Virol., vol. 72 (12): 9706–13, Dec. 1998.

Miller et al., "Differential susceptibility of primary and established human glioma cells to adenovirus infection: *targeting via the epiderman growth factor receptor achieves fiber receptor–independent gene transfer.* " Cancer Res., vol. 58(24): 5738–48, Dec. 1998.
Vanderkwaak et al., "Adenovirus with RGD–modified fiber demonstrates improved gene transfer into ovarian carcinoma cell lines and ovarian primary tumors." Gynecologic Oncology, vol. 72(3): 505, Mar. 1999.
Peng et. al., Viral vector targeting, 1999, Current Opinion in Biotechnology, 10: 454–457.*
Pasqualini et. al., Integrins as receptors for tumor targeting by circulating ligands, 1997, Nature Biotechnology vol. 15:542–546.*
Rajotte, Molecular Heterogeneity of the Vascular Endothelium Revealed by in Vivo Phage Display, 1998, J. Clin. Invest. vol. 102: 430–437.*
Curiel, Strategies to Adapt Adenoviral Vectors for Targeted Delivery, Annals New York Academy of Sciences: 158–171.*
Verma et. al., Gene therapy—promises, problems and prospects, 1997, Nature vol. 389: 239–242.*
Fick et. al., The extent of heterocellular communication mediated by gap junctions is predictive of bystander tumor cytotoxicity in vitro, 1995 Proc.Natl. Acad. Sci. vol. 92: 11071–11075.*
Beck et. al. , The Thymidine Kinase/Ganciclovir–Mediated "Suicide" Effect Is Variabkle in Different Tumor Ceklls; 1995, Human Gene Therapy 6: 1525–1530.*
Jain, Delivery of Molecular and Cellular Medicine To Solid Tumors; 1998, Journal of Controlled Releases 53: 49–67.*
Laquerre et. al., Recombinant Herpes Simplex Virus Type 1 Engineered for Targeted Binding to Erythropoietin Receptor–Bearing Cells, 1998, Journal of Virology:, vol. 72. No. 12:9683–9697.*
Babiss et. al., Cellular Promoters Incorporated into the Adenovirus Genome, 1987, J. Mol. Biol., vol. 193: 643–650..*
Shi et al., Modulation of the Specificity and Activity of a Cellular Promoter in an Adenoviral Vector 1997, Human Gene Theraphy 8: 403–410.*
Anderson, Human gene therapy, 1998, Nature vol. 392: 25–30.*

(List continued on next page.)

*Primary Examiner*—Scott D. Priebe
(74) *Attorney, Agent, or Firm*—Frommer Lawrence & Haug LLP; Thomas J. Kowalski; Deborah Lu

(57) ABSTRACT

A modified adenovirus capable of overcoming the problem of low level of coxsackle-adenovirus receptor (CAR) expression on tumor cells and methods of using such adenovirus are provided. The fiber protein of the adenovirus is modified by insertion or replacement so as to target the adenovirus to tumor cells, and the replication of the modified adenovirus is limited to tumor cells due to mutations in E1a or E1b genes.

12 Claims, 22 Drawing Sheets

OTHER PUBLICATIONS

Hobbs et. al., Regulation If transport pathways in tumor vessels: Role of tumor type and microenvironment; 1998, Proc. Natl. Acad. Sci. vol. 95: 4607–4612.*

Stevenson et. al.; Selective Targeting of Human Cells by a Chimeric Adenovirus Vector Containing a Modified Fiber Protein; 1997, Journal of Virology : 4782–4790.*

Rancourt et. al.; Conditionally replcative adenoviruses for cancer therapy, 1997, Advanced Drug Delivery Reviews 27: 67–81.*

Krasnykh et. al. Characterization of an Adenovirus Vector Containing a Heterologous Peptide Epitope in the HI Loop of the Fi8ber Knob, 1998; Journal of Virology; 1844–1852.*

Alemany et.al.; CAR–binding ablation does not change biodistribution and toxicity of adenoviral vectors, 2001, Gene Therapy 8: 1347–1353.*

Leissner et.al.; Influence of adenoviral fiber mutations on viral encapsidation, infectivity and in vivo tropism, 2001, Gene Therapy 8: 49–57.*

Fox; Investigation of gene therapy begins, 2000, Nature Biotechnology, vol. 18: 143–144.*

Pasqualini et.al.; Integrins as receptors for tumor targeting by circulating ligands, 1997, Nature Biotechnology, vol. 15: 542–546.*

* cited by examiner

INFECTIVITY-ENHANCED CONDITIONALLY-REPLICATIVE ADENOVIRUS AND USES THEREOF

CROSS-REFERENCE TO RELATED APPLICATION

This non-provisional patent application claims benefit of provisional patent application U.S. Ser. No. 60/133,634, filed May 12, 1999.

BACKGROUND OF THE INVENTION

FEDERAL FUNDING LEGEND

This invention was produced in part using funds obtained through a grant from the National Institutes of Health. Consequently, the federal government has certain rights in this invention.

1. Field of the Invention

The present invention relates generally to adenoviral vectors and adenoviral gene therapy. More specifically, the present invention relates to an infectivity-enhanced conditionally replicative adenovirus.

2. Description of the Related Art

Surgery, chemotherapy and radiotherapy constitute the conventional therapies in clinical use to treat cancer. These therapies have produced a high rate of cure in early-stage cancer, but most late-stage cancers remain incurable because they cannot be resected or the dose of radiation or chemotherapy administered is limited by toxicity to normal tissues. An alternative promising approach is the transfer of genetic material to tumor or normal cells as a new therapy itself or to increase the therapeutic index of the existing conventional therapies [1]. In this regard, three main strategies have been developed to accomplish cancer gene therapy: potentiating immune responses against tumors, eliciting direct toxicity to tumors, and compensating the molecular lesions of tumor cells [2].

To achieve the high level of gene transfer required in most cancer gene therapy applications, several viral and non-viral vectors have been designed [13]. Adenoviral vectors have been used preferentially over other viral and non-viral vectors for several reasons, including infectivity of epithelial cells, high titers, in vivo stability, high levels of expression of the transgene, gene-carrying capability, expression in non-dividing cells, and lack of integration of the virus into the genome. In most of the adenoviral vectors used in cancer gene therapy, the transgene substitutes for the early 1 region (E1) of the virus. The E1 region contains the adenoviral genes expressed first in the infectious stage and controls expression of the other viral genes. The early region 3 (E3) gene codes for proteins that block a host's immune response to viral-infected cells and is also usually deleted in vectors used for cancer gene therapy, particularly in immunopotentiating strategies.

E1-substituted, E3-deleted vectors can carry up to 8 kb of non-viral DNA, which is sufficient for most gene therapy applications. E1-substituted, E3-deleted vectors are propagated in packaging cell lines that transcomplement their E1-defectiveness, with production yields of up to 10,000 virion particles per infected cell, depending upon the transgene and its level of expression in the packaging cell. Not all of the viral particles are able to transduce cells or to replicate in the packaging cell line, so bioactivity of a particular vector has been defined as the ratio of functional particles to total particles. This bioactivity varies from 1/10 to 1/1000, depending not only upon the vector, but also upon the methods of purification and quantification [15]. The titer used is the concentration of functional particles, which can be as high as $10^{12}$ per milliliter.

One problem encountered when propagating these vectors to high titers is the recombination of vector sequences with the E1 sequences present in the packaging cell line, thereby producing replication-competent adenoviruses (RCA). This problem has been solved by using packaging cell lines where the E1 gene does not overlap with the vector sequences [16].

The current generation of adenoviral vectors are limited in their use for cancer gene therapy, primarily for three reasons: (1) the vectors are cleared by the reticuloendothelial system, (2) the vectors are immunogenic and/or (3) the vectors infect normal cells. The problem of filtration by the reticuloendothelial system cells, such as macrophages of the spleen or Kupffer cells of the liver, affects adenoviral vectors as well as other viral and non-viral vectors and limits their utility in intravascular administration [19]. The early and late viral genes that remain in E1–E3 deleted vectors may also be expressed at low, but sufficient enough levels such that the transduced cells are recognized and lysed by the activated cytotoxic T lymphocytes. Additionally, a higher viral dose must be injected to reach the entire tumor before a neutralizing immune response develops. The major limitation then becomes the amount of vector that can be safely administered, which will depend upon the capacity of the vector to affect tumor cells without affecting normal cells.

The limitations of adenoviral vectors at the level of infectivity is two-fold. On the one hand, human clinical trials with adenoviral vectors have demonstrated relatively inefficient gene transfer in vivo. This has been related to the paucity of the primary adenovirus receptor, coxsackie-adenovirus receptor (CAR), on tumor cells relative to their cell line counterparts [20–23]. On this basis, it has been proposed that gene delivery via CAR-independent pathways may be required to circumvent this key aspect of tumor biology. On the other hand, adenoviral vectors efficiently infect normal cells of many epithelia. This results in the expression of the transgene in normal tissue cells with the consequent adverse effects. This problem has been addressed by targeting adenoviral vectors to tumor cells at the level of receptor interaction and transgene transcription.

Targeting adenoviral vectors to new receptors has been achieved by using conjugates of antibodies and ligands, in which the antibody portion of the conjugate blocks the interaction of the fiber with the CAR receptor and the ligand portion provides binding for a novel receptor [20]. Receptor targeting has also been achieved b y genetic modification of the fiber [23–26]. Transcriptional targeting of adenoviral vectors has further been demonstrated using tumor-antigen promoters or tissue-specific promoters to control the expression of the transgene [27]. However, these promoters can lose their specificity when inserted in the viral genome and, depending upon the level of toxicity of the transgene, even low levels of expression can be detrimental to normal cells. Thus, for cancer gene therapy, the major issues limiting the utility of adenoviral vectors are the efficiency and specificity of the transduction.

The major limitation found in the use of adenoviral vectors in the clinical setting is the number of tumor cells that remain unaffected by the transgene. A vector that propagates specifically in tumor cells, results in lysis and subsequently allows for transduction of neighbor cells by newly produced virions will increase the number of tumor cells affected by the transgene [28]. A good replicative vector should be weakly pathogenic or non-pathogenic to humans and should be tumor-selective [29]. Efforts have been aimed at improving the safety of replication-competent adenoviruses with the goal of being able to administer much higher doses. One strategy is to transcomplement the E1 defect with an E1-expression plasmid conjugated into the vector capsid [31], which allows a single round of replication thereby producing a new E1-substituted vector with the ability of local amplification and subsequent gene transduction.

Other strategies are designed to obtain vectors that replicate continuously and whose progeny are also able to replicate, but are incapable of propagating in normal cells. In this regard, two approaches have been described that render adenovirus propagation selective for tumor cells: (1) deletions, and (2) promoter regulation [30]. Adenoviral mutants unable to inactivate p53 propagate poorly in cells expressing p53 but efficiently in tumor cells where p53 is already inactive. Based upon this strategy, an adenovirus mutant in which the E1b-55k viral protein was deleted and was unable to bind to p53 was effective in eliminating tumors in preclinical models and is in clinical trials [32]. Controlling viral replication by substituting a viral promoter, such as the E1a promoter, with a tumor associated-antigen promoter, such as the alpha-fetoprotein promoter or the prostate antigen promoter, has been demonstrated [33], and specific lysis of tumors transfected with an adenovirus vector expressing either of the above-mentioned promoters was demonstrated in murine models.

Both approaches have limitations, however. The fact that other viral proteins besides E1b 55K also interact with p53, and because p53 can be necessary for the active release of virus in the later stages of infection may affect the specificity of the vector [37,38]. Another caveat results from using E1a as the only controlled viral gene since E1a-like activity has been found in many tumor cell lines [14,40]. Furthermore, the actual specificity of the above-mentioned promoters for cancer cells, and the fact that promoters inserted in the viral genome can lose their expression specificity, are factors that hindered clinical applications of this approach [39].

Therefore, new methods are clearly needed to achieve more selective therapeutic effects of replication-competent adenoviruses. For these vectors, in parallel to what has been achieved with non-replicative vectors, modification of viral tropism could enhance tumor transduction and tumor selectivity at the level of cell entry, and in this way, realize the full potential of replicative vectors for cancer gene therapy.

The prior art is deficient in adenoviral vectors that are specific for a particular cell type (i.e., do not infect other cell types) and that replicate with high efficiency in only those particular cell types. The present invention fulfills this long-standing need and desire in the art.

SUMMARY OF THE INVENTION

Adenoviral vectors have been widely employed in cancer gene therapy. Their high titers, structural stability, broad infectivity, high levels of transgene expression, and lack of integration have contributed to the utility of this vector. In this regard, adenoviral vectors has been used to transfer a variety of genes to treat cancer such as cytokines, tumor suppresser genes, pro-drug converting genes, antisense RNAs and ribozymes to inhibit the expression of oncogenes, antiangiogenic genes, etc. Despite the promise of adenoviral vectors, results from experimental models and clinical trials have been less than optimal.

Within this context, several specific limitations have been identified. One limitation lies in the poor infectability of primary tumors due to low levels of the primary adenovirus receptor CAR. A second limitation that particularly affects the efficiency of replicative vectors is related to the lack of tumor-specific replication achieved using promoters or mutations. The present invention describes methods to increase adenovirus infectivity based upon modification of the virus tropism. The present invention demonstrates that modification of the adenovirus fiber by genetic manipulation increases infectivity of primary tumors several orders of magnitude due to CAR-independent gene transfer. In addition, selective replication in tumors is described herein, and represents a safe and effective means to lyse and transduce tumors. The present invention further describes a strategy based upon control of the expression of one or more essential early viral genes using tumor-specific promoters.

It is a goal of the present invention to improve the infectivity and specificity of conditional replicative vectors, thereby improving their therapeutic utility and efficacy.

One object of the present invention is to provide adenoviral vectors that possess enhanced infectivity to a specific cell type (i.e., that are not limited to CAR-dependent cell entry) and that replicate with high efficiency in only those cell types.

In an embodiment of the present invention, there is provided an infectivity-enhanced conditionally-replicative adenovirus. This adenovirus possesses enhanced infectivity towards a specific cell type, which is accomplished by a modification or replacement of the fiber of the adenovirus. The modification is accomplished by introducing a fiber knob domain from a different subtype of adenovirus, introducing a ligand into the HI loop of the fiber knob, or replacing the fiber with a substitute protein which presents a targeting ligand. Additionally, the adenovirus has at least one conditionally regulated early gene, such that replication of the adenovirus is limited to the specific cell type.

In yet another embodiment of the present invention, there is provided a method of enhanced-infectivity conditionally-replicative adenoviral gene therapy in an individual in need of such treatment. This method comprises the steps of: administering to an individual a therapeutic dose of an infectivity-enhanced conditionally-replicative adenovirus. This adenovirus possesses enhanced infectivity towards a specific cell type, which is accomplished by a modification or replacement of the fiber of the adenovirus. The modification is accomplished by introducing a fiber knob domain from a different subtype of adenovirus, introducing a ligand into the HI loop of the fiber knob, or replacing the fiber with a substitute protein which presents a targeting ligand. The adenovirus also has at least one conditionally regulated early gene, such that replication of the adenovirus is limited to the specific cell type.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 1 shows that an anti-knob Fab-FGF2 conjugate enhances cell transduction.

FIG. 3 shows the HI loop of the fiber as a domain to insert ligand for retargeting adenoviruses.

FIG. 14 shows replication of Ad5dl312 and oncolytic effect in tumor cells without IL-6 addition. Ovarian carcinoma cells (OVCAR-3) were infected with E1-a deleted AD5dl312, wild type or E4-deleted Ad5dl1014 (MOI=10).

FIG. 17 shows the analyses of adeno viral DNA.

FIG. 19 shows oncolytic potency of the RGD-modified virus.

FIG. 20 shows in vivo oncolysis by high and low doses of infectivity-enhanced CRAds.

DETAILED DESCRIPTION OF THE INVENTION

Figure 1A:
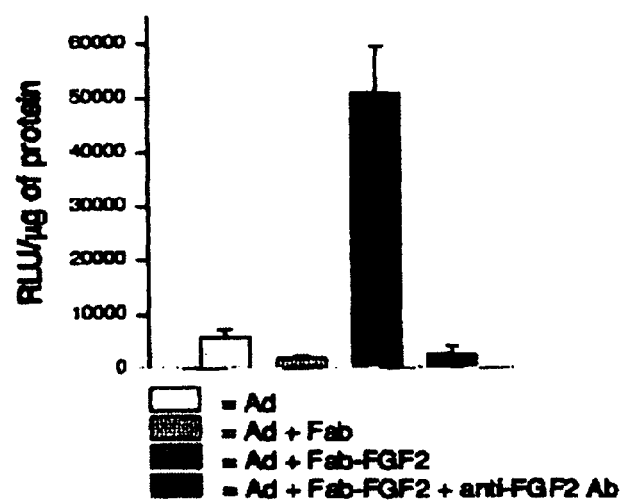
FIG. 1A shows that AdCMVluc ($5 \times 10^7$ pfu) was preincubated with 1.44 µg of Fab or 1.94 µg of Fab-FGF2. SKOV3 cells (24,000 cells per well in 24-well plates) were infected with control vector or with the vector complexes (MOI of 50). Inhibition was performed by adding a polyclonal anti-FGF2 to the complex before infection. Luciferase activity in cell lysates was assayed 24 h after infection. The mean of triplicate experiments is shown.

The present invention addresses the two major limitations of replicative adenoviral agents (viruses and vectors) in their application to cancer gene therapy, i.e., the efficacy of transduction and the specificity of replication. Adenovirus binds to the coxsackievirus-adenovirus receptor, CAR, in the cellular membrane using the C-terminal globular domain of the viral fiber, the knob [41]. Since a limited amount of coxsackievirus-adenovirus receptor is present in tumors, one means to enhance infectivity would be to provide additional binding pathways [20,21]. Therefore, two methods have been developed to modify adenovirus binding. The first method uses a Fab fragment of an anti-knob antibody conjugated to a ligand of a cellular receptor, while the second method comprises direct genetic modification of the knob sequence.

One important advantage of direct genetic modification is that the progeny will carry the modified fiber, thereby retaining the replicative virus' enhanced infectivity trait through the amplification cycles. Wickman et al. have generated adenoviruses with chimeric fibers in which the ligand is connected to the carboxyl terminal position of the fiber

[26]. This carboxyl terminal location is not always appropriate because the addition of more than 20–30 heterologous amino acid residues can result in the loss of fiber trimerization and binding to the capsid. Furthermore, the three-dimensional structure of the fiber indicates that the carboxyl terminal end points towards the virion, and therefore, away from the cell surface [42]. For these reasons, the HI loop was used herein as an exposed and amenable site for the incorporation of exogenous sequences.

With regard to the efforts to increase the specificity a t the level of virus replication, methods have been developed to confer regulated-replication or conditional-replication competency to adenoviral vectors based upon complementing, in trans, the essential early genes that are missing in the replication-defective vectors. In this way, E1-deleted and E4-deleted vectors have been transcomplemented by conjugating them to E1 or E4 expression plasmids [43,44]. This method enables the vectors to replicate, thereby augmenting their transduction ability. Methods have also been explored that allow the continuous replication of the vector, such as using the E1a-like activity provided by interleukin 6 to enable replication of E1a-deleted vectors.

It has been recognized that the major limitation in several strategies of cancer gene therapy resides in the need to transduce the majority of cells of a tumor. With the exception of a limited bystander effect described in some strategies, the cells that are left untransduced will jeopardize and reduce any therapeutic effect. Adenoviral vectors are limited in this regard by the paucity of its receptor, CAR, in tumors [20–23]. It is a goal of the present invention to improve the infectivity of adenoviral vectors by providing additional pathways to cell binding besides CAR. Previous data has shown that modification of the HI loop of the fiber is a feasible strategy to add new ligand motifs into the fiber. An RGD motif has already been incorporated into the fiber of regular E1-deleted vectors and been shown to enhance the therapeutic effects in vivo.

The present invention describes the incorporation of modified fiber into replicative adenoviral vectors. The present invention further describes methods to enhance the specificity of the replication of these replicative adenoviral vectors. The current methods of mutating E1, or regulation of E1 with tumor-specific promoters, are both very rational approaches, but may prove not selective enough for several reasons. In the case of E1 deletions, the main limitation lies in incomplete knowledge of the role of these proteins in the viral replicative cycle and in controlling the cell cycle. For example, adenovirus may use a p53-dependent mechanism to release the progeny from the infected cell [38]. This would predicate a positive role for p53 in virus production and would reduce the yields of virus in p53-deficient cells. On the other hand, other viral proteins besides E1-55K may block p53 function, such as E4, and this would allow the 55K- to replicate in p53+ cells [37]. In any case the specificity of a 55K- for p53-defective cells is controversial [35,36]. Regarding to strategies based on regulation of E1 it is a concern that promoters can lose certain degree of specificity when inserted into the viral genome [39]. The presence of E1-like activity in uninfected cells could also pose a problem for the specificity achieved with both vectors. In this regard, some replication of E1 vectors has been observed in many different cell lines [40].

Therefore, it is desirable to improve the replication selectivity of replicative adenoviral vectors for tumors by achieving tumor-selective regulation of key early genes other than E1, such as E2 or E4. An adenovirus-polylysine-DNA transcomplementation system has been developed as a means to evaluate replication. This replication-enabling system is used to analyze the efficacy and specificity of tumor-specific replication mechanisms based on the regulation of the E4 or E2 genes. In the transcomplementation system, plasmids encoding E2 or E4 under the control of different tumor-specific promoters are used to screen for mechanisms that confer selective replication. Ultimately, selective replication will involve the incorporation of the regulated E4 or E2 into the viral genome to achieve continuous replication. Accordingly, after the tumor-selective replication has been demonstrated, these regulatory mechanisms are incorporated into a single viral vector. Optimally, these regulatory mechanisms are combined with the fiber modification described herein to enhance infectivity.

Initial tumor models are based on cell lines with differential expression of the PSA protein: LNCaP and DU145. Tumors derived from lung adenocarcinoma cell lines and ovarian cell lines are used to evaluate viruses with promoters such as Carcinoembryonic antigen (CEA) or secretory leukoprotease inhibitor (SLPI). Therapeutic effects are only observed in tumors derived from the cell lines that allow the expression of the tumor-specific controlled E4 or E2, that is, replication of the virus. In these permissive cell lines, higher therapeutic advantage is observed for the RGD-modified virus relative to the unmodified virus.

The present invention is directed towards an infectivity-enhanced conditionally-replicative adenovirus. This adenovirus possesses enhanced infectivity towards a specific cell type, which is accomplished by a modification or replacement of the fiber of a wildtype adenovirus and results in enhanced infectivity relative to the wildtype adenovirus. The adenovirus also has at least one conditionally regulated early gene, such that replication of the adenovirus is limited to the specific cell type. Preferably, the cell is a tumor cell.

Preferably, the modification or replacement of the fiber results in CAR-independent gene transfer. Generally, the modification is accomplished by introducing a fiber knob domain from a different subtype of adenovirus. The fiber can also be modified by introducing a ligand into the HI loop of the fiber knob, or replacing the fiber with a substitute protein which presents a targeting ligand. Representative ligands include physiological ligands, anti-receptor antibodies and cell-specific peptides. Additionally, the ligand may comprise a tripeptide having the sequence Arg-Gly-Asp (RGD), or more specifically, a peptide having the sequence CDCRGD-CFC (SEQ ID No. 1).

Generally, the fiber substitute protein associates with the penton base of the adenovirus. Structurally, the fiber substitute protein is preferably a rod-like, trimeric protein. It is desirable for the diameter of the rod-like, trimeric protein to be comparable to the native fiber protein of wild type adenovirus. It is important that the fiber substitute protein retain trimerism when a sequence encoding a targeting ligand is incorporated into the carboxy-terminus. In a preferred aspect, a representative example of a fiber substitute protein is T4 bacteriophage fibritin protein. In a preferred embodiment, the fiber substitute protein comprises: a) an amino-terminal portion comprising an adenoviral fiber tail domain; b) a chimeric fiber substitute protein; and c) a carboxy-terminal portion comprising a targeting ligand. More generally, the fiber substitute protein can be selected from the group consisting of trimeric structural proteins, trimeric viral proteins and trimeric transcription factors. Other representative examples of fiber substitute proteins include isoleucine trimerization motif and neck region peptide from human lung surfactant D. Preferably, the fiber substitute protein has a coiled coil secondary structure. The secondary structure provides stability because of multiple interchain interactions. The fiber substitute protein does not have to be a natural protein. In fact, a person having ordinary skill in this art would be able to construct an artificial protein. Preferably, such an artificial fiber substitute protein would have a coiled coil secondary structure.

The early gene may be conditionally regulated by means consisting of a tissue-specific promoter operably linked to an early gene (e.g., E1, E2 and/or E4) and a mutation in an early gene (e.g., E1, E2 and/or E4). Representative tissue-specific promoters are the prostate specific antigen (PSA), Carcinoembryonic antigen (CEA), secretory leukoprotease inhibitor (SLPI), and alpha-fetoprotein (AFP).

Additionally, the adenovirus may carry a therapeutic gene in its genome. In conjunction with the above-mentioned therapeutic gene, a method of providing gene therapy to an individual in need of such treatment is disclosed herein, comprising the steps of: administering to the individual an effective amount of an infectivity-enhanced conditionally-replicative adenovirus. When the therapeutic gene carried by the adenovirus is, for instance, a herpes simplex virus thymidine kinase gene, the present invention further provides for a method of killing tumor cells in an individual in need of such treatment, comprising the steps of: pretreating the individual with an effective amount of an infectivity-enhanced conditionally-replicative adenovirus expressing the TK gene; and administering ganciclovir to the individual. Generally, the individual has cancer.

The present invention is also directed towards a method of infectivity-enhanced and conditionally-replicative adenoviral gene therapy in an individual in need of such treatment, comprising the steps of: administering to the individual a therapeutic dose of an infectivity-enhanced conditionally-replicative adenovirus. Representative routes of administration are intravenously, intraperitoneally, systemically, orally and intratumorally. Generally, the individual has cancer and the cell is a tumor cell.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from a mRNA transcript. An "exon" is an expressed sequence transcribed from the gene locus, whereas an "intron" is a non-expressed sequence that is from the gene locus.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with other proteins which can upregulate or downregulate expression of a specific gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes.

Prokaryotic promoters contain Shine-Dalgarno sequences in addition to the −10 and −35 consensus sequences.

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

Primers are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to enzymes which cut double-stranded DNA at or near a specific nucleotide sequence.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "host" is meant to include not only prokaryotes but also eukaryotes such as yeast, plant and animal cells. A recombinant DNA molecule or gene can be used to transform a host using any of the techniques commonly known to those of ordinary skill in the art. Prokaryotic hosts may include *E. coli, S. tymphimurium, Serratia marcescens* and *Bacillus subtilis*. Eukaryotic hosts include yeasts such as *Pichia pastoris*, mammalian cells and insect cells, and more preferentially, plant cells, such as *Arabidopsis thaliana* and *Tobaccum nicotiana*.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

As used herein, the terms "conditionally regulated" and "conditionally-replicative" refer to the expression of a viral gene or the replication of a virus or a vector, wherein the expression of replication is dependent (i.e., conditional) upon the presence or absence of specific factors in the target cell.

As used herein, the term "early genes" refers to those adenoviral genes expressed prior to the onset of adenoviral DNA replication.

As used herein, the term "CAR-independent infectivity" refers to the entry of adenovirus into a cell by receptors different from the coxsackie-adenovirus receptor (CAR).

As used herein, the term "RGD-integrin interaction" refers to the arginine-glycine-aspartic acid (RGD) residues in a peptide binding to the integrin receptor molecules.

As used herein, the term "replication-competent adenoviruses" refers to an adenovirus capable of replication (i.e., an adenovirus that yields progeny).

As used herein, the term "fiber substitute protein" is a protein that substitutes for fiber and provides three essential features: trimerizes like fiber, lacks adenoviral tropism and has novel tropism.

It is specifically contemplated that pharmaceutical compositions may be prepared using the novel adenovirus of the present invention. In such a case, the pharmaceutical composition comprises the novel adenovirus of the present invention and a pharmaceutically acceptable carrier. A person having ordinary skill in this art would readily be able to determine, without undue experimentation, the appropriate dosages and routes of administration of this adenovirus of the present invention. When used in vivo for therapy, the adenovirus of the present invention is administered to the patient or an animal in therapeutically effective amounts, i.e., amounts that eliminate or reduce the tumor burden. It may be administered parenterally, preferably intravenously, but other routes of administration will be used as appropriate. The dose and dosage regimen will depend upon the nature of the cancer (primary or metastatic) and its population, the characteristics of the particular immunotoxin, e.g., its therapeutic index, the patient, the patient's history and other factors. The amount of adenovirus administered will typically be in the range of about $10^{10}$ to about $10^{11}$ viral particles per patient. The schedule will be continued to optimize effectiveness while balanced against negative effects of treatment. See Remington's Pharmaceutical Science, 17th Ed. (1990) Mark Publishing Co., Easton, Pa.; and *Goodman and Gilman's: The Pharmacological Basis of Therapeutics* 8th Ed (1990) Pergamon Press; which are incorporated herein by reference. For parenteral administration, the adenovirus will most typically be formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The immunotoxin will typically be formulated in such vehicles at concentrations readily recognizable to those having ordinary skill in this art.

The following examples are given for the purpose of illustrating various embodiments of the invention and are not meant to limit the present invention in any fashion:

EXAMPLE 1

Figure 1B:
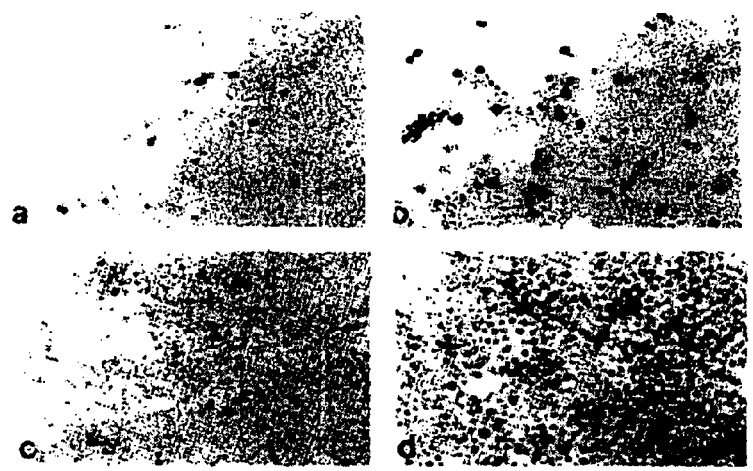
FIG. 1B shows that AdCMVLacZ was complexed with Fab-FGF2 conjugate as in FIG. 1A. SKOV3 cell were infected with control vector (a, c) or complexed vector (b, d) at MOI of 5 (a, b) or 50 (c, d) and stained with X-gal 24 h after infection.

Enhanced Tumor Transduction with Adenoviral Vectors Modified with a Ligand Attached to the Fiber As a first approach towards enhancing the infectivity of adenoviral vectors and to demonstrate the tumor transduction advantage of vectors with altered tropism over unmodified vectors, an anti-fiber antibody conjugated to fibroblast growth factor (FGF2) was used. The Fab portion of the anti-knob antibody, 1D6.14, which is capable of blocking the interaction of the fiber with its cognate cellular receptor, was chemically conjugated to FGF2. The resulting Fab-FGF2 conjugate was complexed with adenoviral vectors expressing luciferase or β-galactosidase reporter genes to compare the transduction efficiency of the modified and unmodified vectors. Vector modification increased the level of gene expression more than 9-fold, as measured by luciferase activity (FIG. 1A), largely due to transduction of a greater percentage of target cells as seen by β-galactosidase staining (FIG. 1B). This experiment clearly demonstrates that a retargeted adenoviral vector can overcome the inefficacious transduction observed in certain cell lines transduced poorly by adenoviral vectors.

Figure 2:
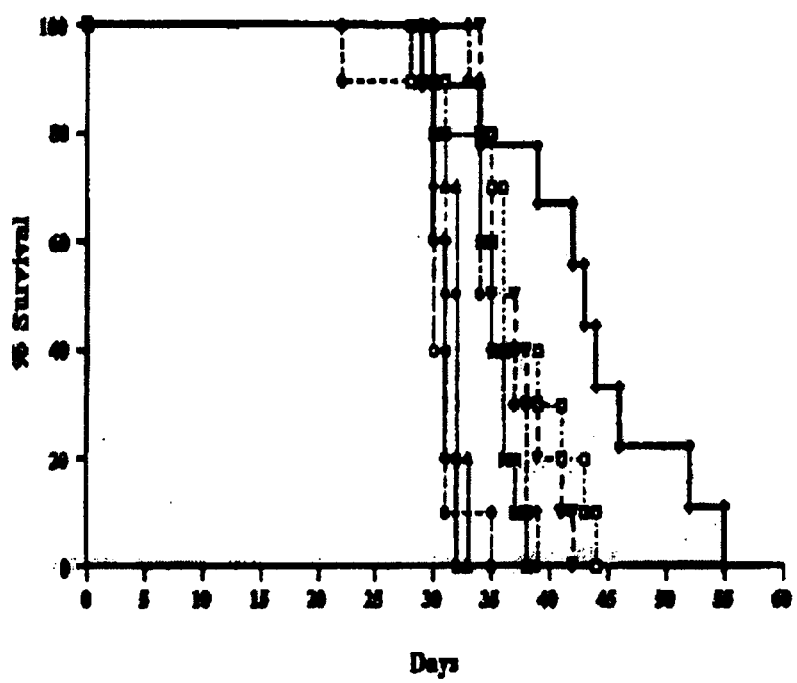
FIG. 2 shows that Fab-FGF2 retargeting augments in vivo therapeutic benefit of the AdCMVHSV-TK vector. Five days after i.p. inoculation of $2 \times 10^7$ SKOV3 cell in SCID mice, $2 \times 10^8$ or $2 \times 10^9$ pfu of AdCMVTK alone or complexed with FGF2 were injected i.p. Forty-eight h later, half of the mice were treated with GCV (50 mg/kg body weight) for 14 days. Survival was monitored daily.

To compare the therapeutic effect of an FGF2-modified vector to an unmodified vector in established tumors, the conjugate was then mixed with an adenovirus expressing HSV-TK (AdCMVHSV-TK). Treatment with the modified vector of SKOV3 ovarian carcinomas established in nude mice followed by administration of the prodrug, ganciclovir, resulted in a significant prolongation of survival when compared with the unmodified vector plus ganciclovir (FIG. 2). Thus, retargeting can increase the in vivo therapeutic effect of adenoviral vectors against tumors. It is clear that the infectivity of tumors by unmodified adenovirus is not optimal and modification of the capsid to alter the tropism of the virus is a direct approach to increase this infectivity.

EXAMPLE 2

Figure 3A:
FIG. 3A shows the knob trimer viewed along the three-fold symmetry axis (Reproduced from Xia et al. [42]).
Figure 3B:
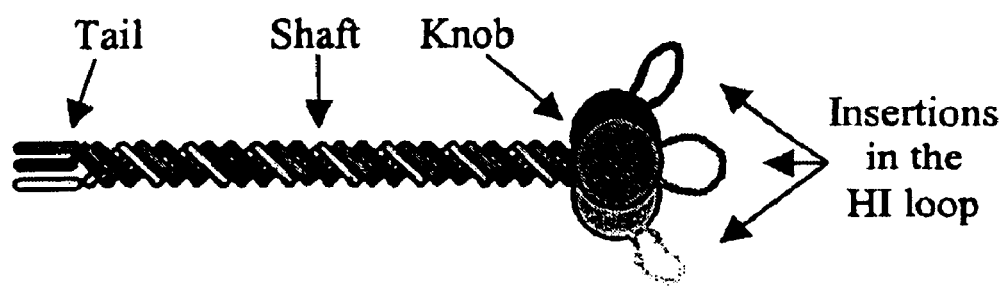
FIG. 3B shows the localization of targeting ligands within the fiber molecule.

Genetic Modification of the HI Loop of the Fiber Provides Enhanced Infectivity to Adenoviral Vectors The Fab-ligand conjugation method described in Example 1 only modifies the tropism of the vector prepared for inoculation. In the context of a replicative vector, it is advantageous to modify the tropism of the vector that replicates in the tumor as well. With this rationale, a genetic modification of the fiber is necessary for replicative vectors because it is carried over to the progeny. As a simple and potent strategy for retargeting, the sequence of the fiber was genetically modified. Based on the three-dimensional model of the fiber knob [42], targeting ligands were inserted into the HI loop of the fiber (FIG. 3). This loop is flexible, exposed on the outside of the knob, is not involved in fiber trimerization and its variable length in different Ad serotypes suggests that insertions or substitutions do not affect the fiber stability.

As a ligand to introduce into the HI loop of the fiber knob, the sequence coding for an RGD peptide, CDCRGDCFC (SEQ ID No: 1), was chosen. This RGD sequence is known to target tumors by binding with high affinity to several types of integrins [45,46]. It was hypothesized that an adenoviral vector able to bind via fiber-RGD/integrin interaction would not depend upon the presence of the CAR receptor in tumors to be effective, and would therefore target tumors more efficiently than the unmodified vector counterpart.

The DNA sequence encoding the peptide was cloned into the EcoRV site of the knob domain in a plasmid containing the fiber sequence. The wild type fiber of an E1,E3-deleted adenoviral vector expressing the luciferase gene, AdCMVLuc, was replaced with the RGD-modified fiber by homologous recombination in bacteria [47]. After homologous recombination, the genome of the new adenoviral vector was released from the plasmid backbone by digestion with PacI. To use the firefly luciferase gene, the internal PacI site of this gene was eliminated by introducing a silent mutation. The plasmid obtained as a result of these DNA recombinations was then utilized for transfection of 293 cells to rescue Ad5lucRGD. The presence of RGD in the virus was confirmed by PCR as well as by cycle sequencing of viral DNA isolated from CsCl-purified virions of Ad5lucRGD.

Figure 4A:
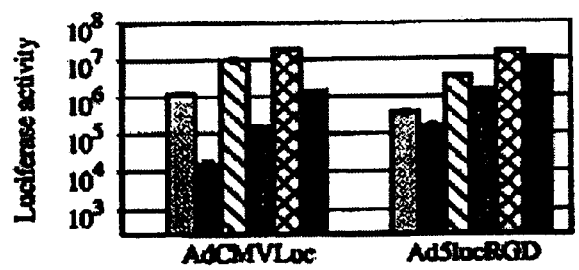
FIG. 4 shows adenovirus-mediated gene transfer to various human cell lines. 293 (FIG. 4A), human vascular endothelial cells (HUVEC) (FIG. 4B) or Rhabdomyosarcoma (RD) (FIG. 4C) cells preincubated for 10 min at room temperature in medium containing recombinant Ad5 fiber knob at 100 µg/ml were then exposed for 30 min at room temperature to AdCMVLuc or Ad5lucRGD in DMEM/F12 at 1, 10 or 100 pfu/cell. The unbound virus was aspirated and complete medium was added. After incubation at 37° C. for 30 hours, the cells were lysed and the luciferase activity in relative light units (rlu) was determined. Background luciferase activities detected in mock infected cells were 261, 223, and 163 rlu for 293, HUVEC and RD cells, respectively. These activities were subtracted from all readings obtained with the corresponding cell line. Each point represents the mean of three determinations±SD.
Figure 4B:
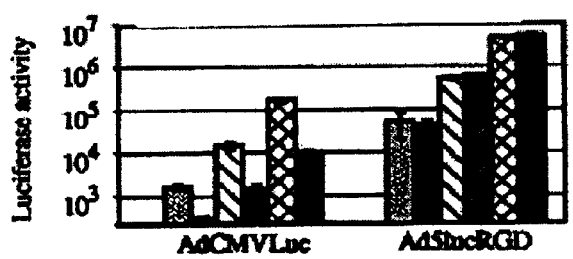
Figure 4C:
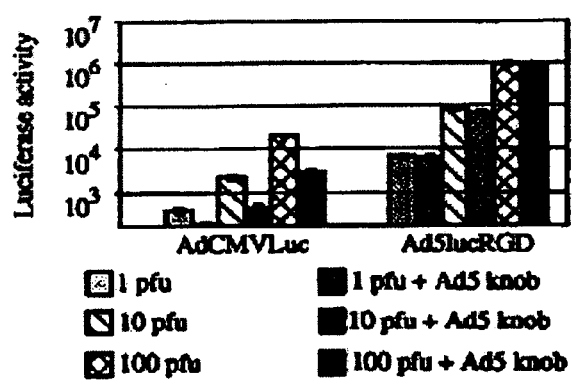

To demonstrate that the genetic modification of the fiber was able to confer CAR-independent infectivity to the modified vector, the unmodified AdCMVLuc and the modified Ad5lucRGD vectors were used to transduce 293, HUVEC, and RD cell lines, which express high, moderate, and low levels of CAR, respectively. The CAR-independent infection was further analyzed using competitive inhibition by recombinant Ad5 fiber knob protein, known to efficiently block virus binding to CAR receptor. Luciferase expression in 293 cells mediated by the unmodified virus, AdCMVLuc, was efficiently blocked by recombinant knob protein (FIG. 4A). Depending on the multiplicity of infection (MOI) used, knob protein blocked 85% to 93% of luciferase activity in AdCMVLuc-transduced cells. In contrast, the same concentration of knob was able to block only 40% to 60% of Ad5lucRGD-mediated gene expression in 293 cells, indicating that in addition to the fiber-CAR interaction utilized by the wild type Ad5, Ad5lucRGD is capable of using an alternative, CAR-independent, cell entry pathway. Of note, the contribution of that alternative mechanism of cell binding was quite significant, providing 40% to 60% of overall gene transfer to 293 cells. Luciferase expression in HUVEC cells transduced with Ad5lucRGD was about 30-fold higher than with AdCMVLuc (FIG. 4B). The effect of Ad5 fiber knob on AdCMVluc-mediated transduction was less dramatic than in 293 cells, consistent with a relative lack of CAR in the HUVEC. Most importantly, recombinant knob protein did not inhibit the levels of luciferase expression directed by Ad5lucRGD. The luciferase activity detected in RD cells transduced with AdCMVluc was extremely low: at an MOI of one pfu/cell, it was almost equal to the background level of mock-infected cells (FIG. 4C). In contrast, the level of transgene expression achieved with Ad5lucRGD was 16- to 47-fold higher than with AdCMVLuc, and expression was not inhibited by the fiber knob.

These experiments clearly showed that incorporation of the RGD peptide into the fiber of AdSlucRGD resulted in dramatic changes in virus-to-cell interaction by providing an alternative CAR-independent cell attachment pathway. Of note, the insertion of the RGD sequence in the HI loop did not abrogate the CAR-mediated entry pathway, so the modified vector has a two independent mechanism to bind to the cells. As the present invention shows, this contributes to the enhanced infectivity of the modified vector in all cell lines and tumors tested.

EXAMPLE 3

Enhanced Tumor Transduction via RDG-fiber Modification

To determine if the RGD sequence incorporated into the HI loop of the fiber could increase the infectivity of tumors, the ability of the modified vector to deliver genes to cultured human ovarian cancer cells was examined. Characterization of two cell lines, SKOV3.ip1 and OV-4, by flow cytometry showed that they both express moderate-to-high levels of $\alpha v\beta 3$ and $\alpha v\beta 5$ integrins. SKOV3.ip1 also expresses a high level of CAR, whereas OV-4 only modestly expresses CAR.

Figure 5A:
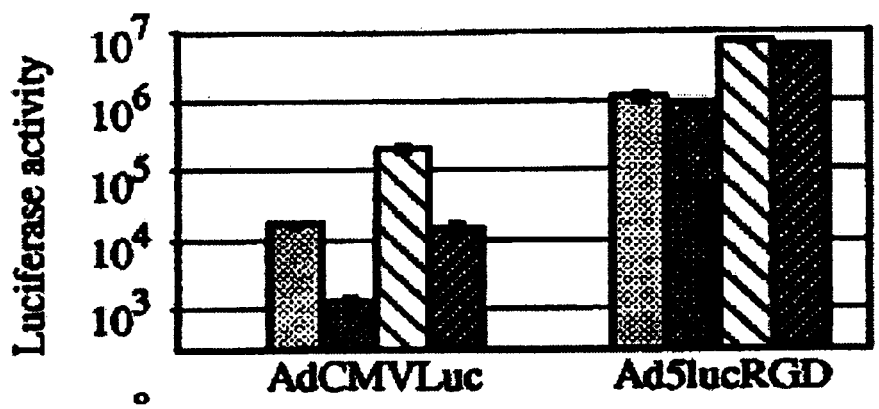
FIG. 5 shows a comparison of the gene transfer efficiencies to cultured ovarian cancer cells mediated by AdCMV-Luc and Ad5lucRGD. Human ovarian cancer cells SKOV3.ip1 (FIG. 5A) and OV-4 (FIG. 5B) were transduced with AdCMVluc or Ad5lucRGD at an MOI of 1 or 10 pfu/cell essentially as described in FIG. 4 for 293, HUVEC and RD cells. Recombinant Ad5 fiber knob protein was added to cells prior to infection with the virus. Each data point is the average of three independent measurements obtained in one experiment.
Figure 5B:
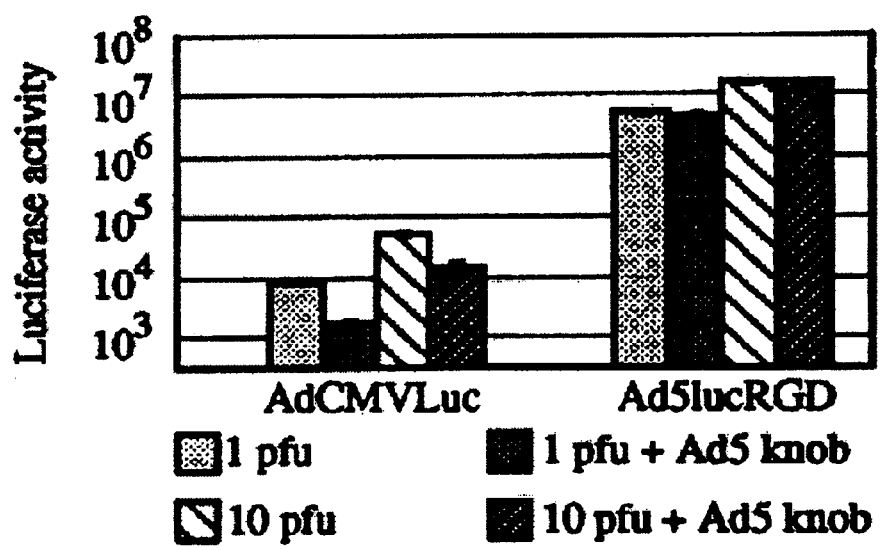

The incorporation of recombinant RGD-containing fiber protein in the Ad5lucRGD vector dramatically improved the ability of the virus to efficiently transduce these cells (FIG. 5A). At different MOIs tested, Ad5lucRGD-transduced cultures of SKOV3.ip1 cells showed 30-fold to 60-fold increase in luciferase activity compared to cells transduced with control virus. Interestingly, while the purified fiber knob blocked over 90% of AdCMVLuc-mediated gene transfer, it could only block 20% of luciferase activity in Ad5lucRGD-treated cells, indicating a majority of CAR-independent entry mechanisms for Ad5lucRGD. In OV-4 cells, the transduction efficiency achieved with the RGD-modified vector was 300- to 600-fold higher than the unmodified one (FIG. 5B). Again, when the fiber knob was used as an inhibitor of CAR-mediated cell entry, it did not have any significant effect on Ad5lucRGD-mediated gene delivery, strongly suggesting that this virus primarily utilizes RGD-integrin interaction to bind to target cells.

The utility of the Ad5lucRGD vector was next evaluated in the context of primary tumor cells. In this regard, recent human clinical trials have pointed out the disparity between the efficacy of adenoviral vectors in various model systems and in the clinical context, where rather low transduction efficiencies have been noted [20–23]. As integrins have been shown to be frequently overexpressed by various epithelial tumors, vector targeting to these cell surface receptors provides a means to achieve CAR-independent gene transfer [46].

Figure 6A:
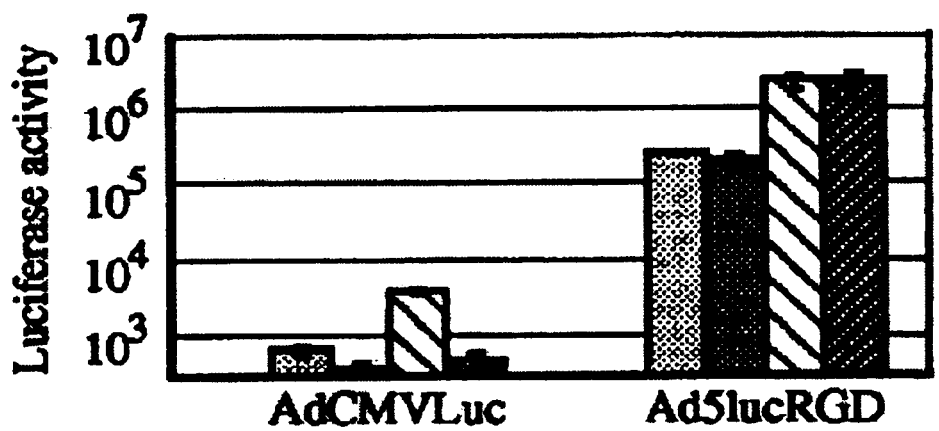
FIG. 6 shows transduction of primary cells isolated from ascites obtained from ovarian cancer patients. Cells isolated from ascites of two (FIGS. 6A and B) ovarian cancer patients were transduced with AdCMVLuc or Ad5lucRGD at MOI of 1 or 10 in the presence or absence of blocking Ad5 fiber knob protein. The data points represent the mean of three independent determinations.
Figure 6B:
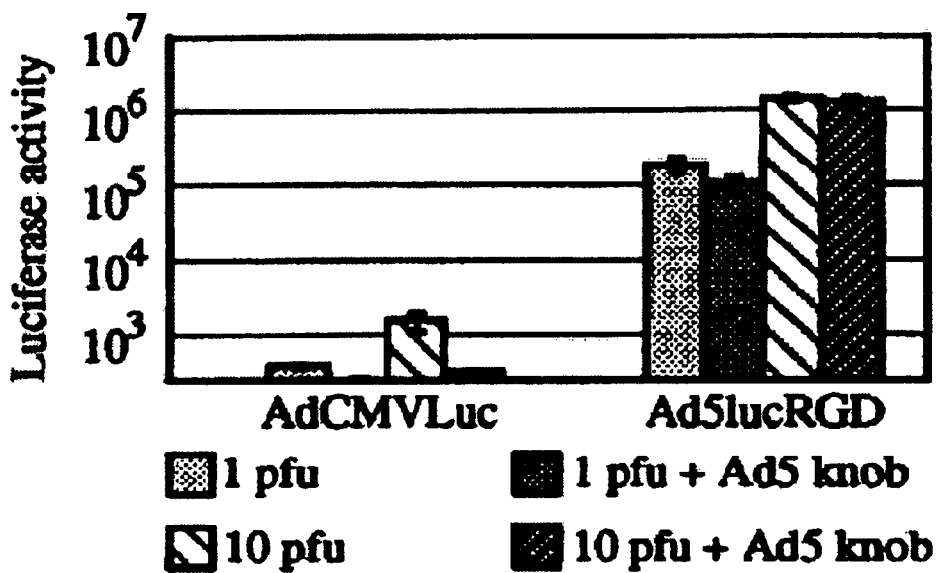

In the experiments described herein, ovarian cancer cells obtained from two patients were treated with either Ad5lucRGD or AdCMVLuc in the presence or absence of blocking knob protein. Luciferase expression in cells treated with AdCMVLuc was extremely low (FIG. 6), thereby indicating inability of adenoviral vectors containing unmodified fibers to efficiently infect ovarian cancer cells. Strong inhibition by the fiber knob on AdCMVLuc-mediated luciferase expression suggests that the fiber-CAR interaction is the only pathway this virus can use to infect this type of cell. In contrast, Ad5lucRGD directed levels of transgene expression two- to three-orders of magnitude higher than those detected in AdCMVLuc-transduced cells. The knob blocked 20% of the gene transfer at an MOI of 1 pfu/cell, and no effect was observed at an MOI of 10 pfu/cell.

Figure 7:
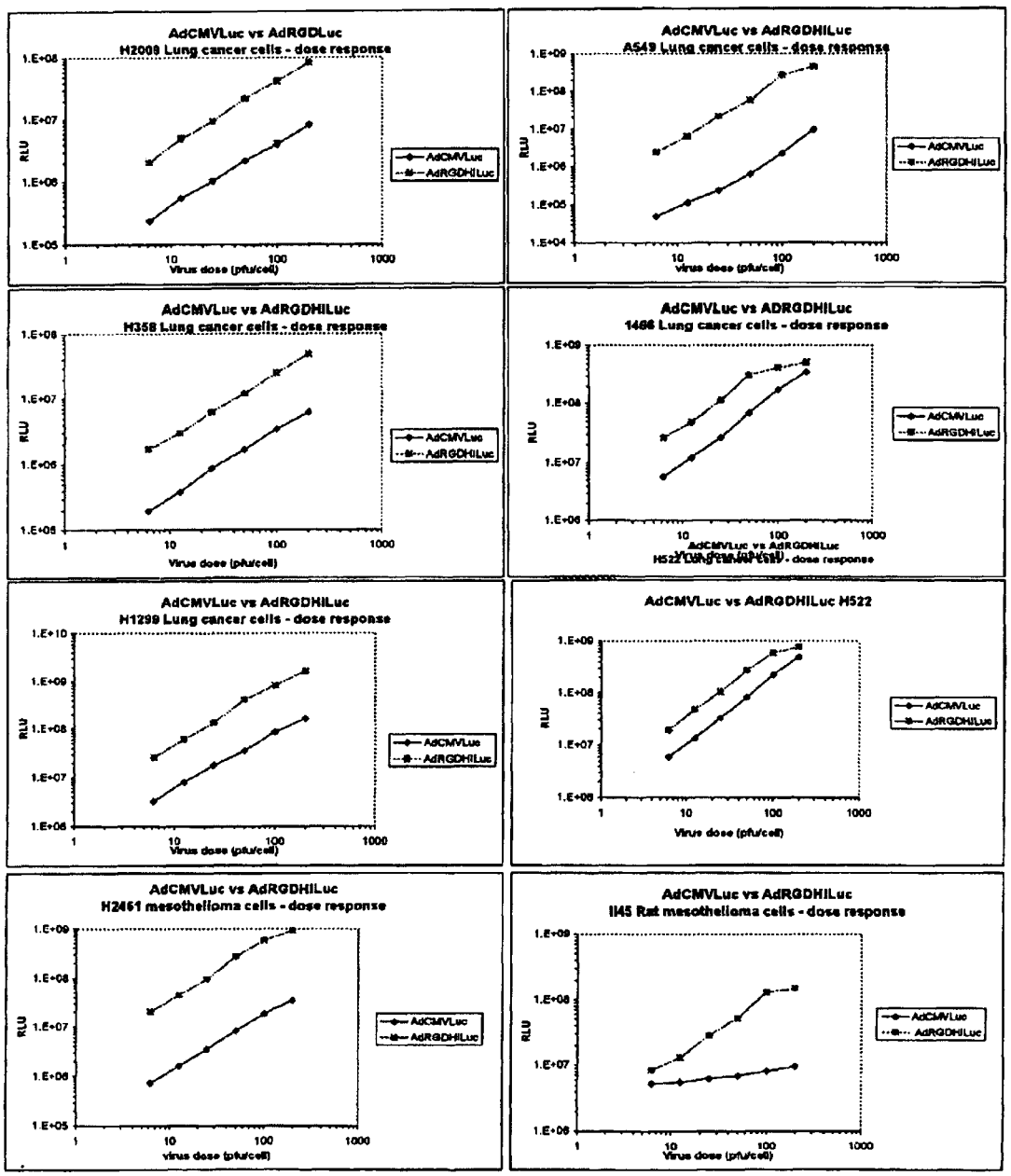
FIG. 7 shows a comparison of expression of luciferase achieved with the RGD-modified vector, AdRGDluc versus the non-modified vector AdCMVluc. For each cell line, 25,000 cells were infected at different MOIs and the luciferase expression was measured 36 h after infection. The mean value of three wells is shown.

The observations of enhanced infectivity have been extended to other tumor cell types besides ovarian carcinoma. In six human non-small cell lung adenocarcinoma cell lines, one human mesothelioma cell line, and one rat mesothelioma cell line, the luciferase expression level achieved with the RGD-modified vectors was always higher than the level achieved with the non-modified vector at a variety of different MOIs (FIG. 7).

Figure 8A:
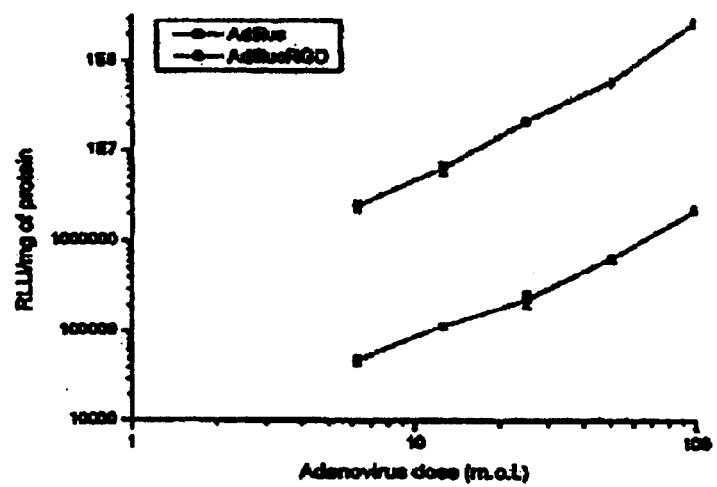
FIG. 8 shows enhancement of adenovirus infectivity by RGD modification of the fiber knob. Triplicates of A549 cells (panel A) and LNCaP cells (panel B) were transduced with increasing doses of either Ad5luc or Ad5lucRGD. After 36 h, cell transduction was determined by luciferase assay. The data are presented as relative light units (RLU) normalized to mg of cellular protein. The results show an infectivity advantage of the RGD modified vector over the non-modified one in both cell lines.
Figure 8B:
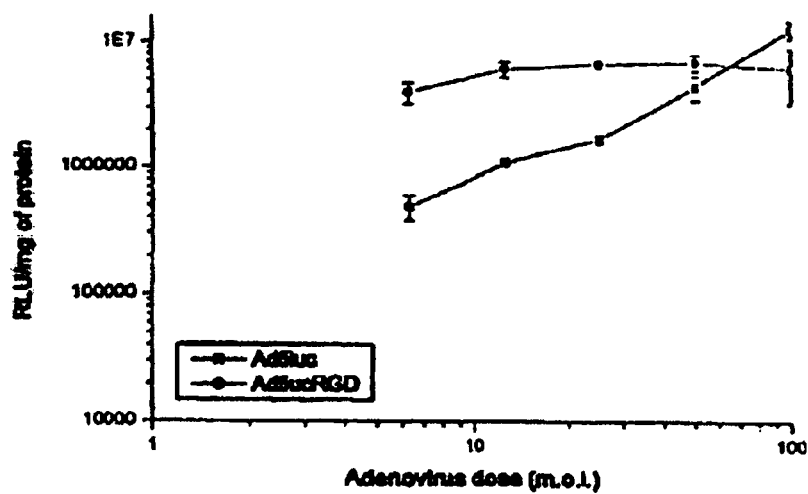

The increase in transduction was also observed in A549 lung adenocarcinoma cells and LNCaP prostate carcinoma cells (FIG. 8). In both cell lines the RGD modified vector showed a n infectivity advantage over the non-modified counterpart. The major difference was observed in A549 cells, showing a 100-fold increase in infection, whereas LNCaP cells showed 10-fold increase. In LNCaP, the major differences were observed at lower multiplicities of infection, likely indicating that the integrin-mediated pathway was saturated.

Figure 9:
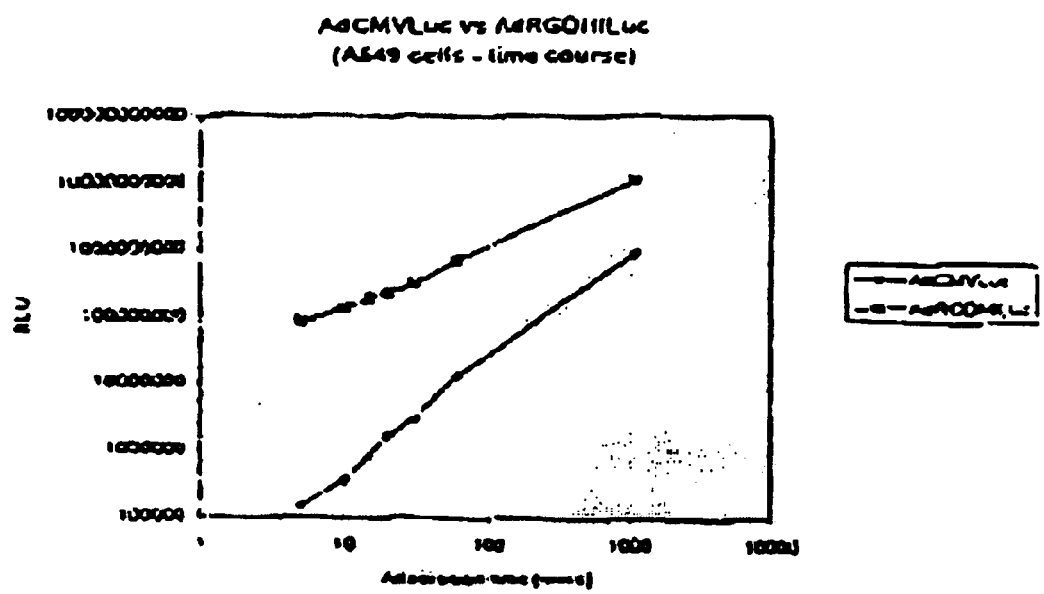
FIG. 9 shows luciferase expression levels achieved with the RGD-modified vector, AdRGDluc, versus the non-modified vector, AdCMVluc, depending on the adsorption time. A549 lung adenocarcinoma cells ($10^5$/well) were incubated with an MOI of 100 pfu/cell during different times (a larger amount of cells and a higher MOI were used relative to the previous experiment in order to achieve detectable expression at short adsorption times). After the adsorption time, the cells were washed three times with PBS and complete medium was added. Luciferase was measure 36 h after infection. The mean value of three wells is shown.

The increased efficacy of infection of the RGD-modified vector was also measured in time course experiments in which the incubation time of the virus with the cells was limited. The transduction efficiency was always better with the modified vector and the differences were more marked at shorter times of infection: the RGD-modified vector produced a 1000-fold greater luciferase expression when only 7 minutes of adsorption were allowed (FIG. 9). At longer adsorption times, the differences between the modified and non-modified vectors were reduced to 10-fold. This difference could have important implications in adenoviral-mediated gene therapy because the time of exposure of the vector to the tumor target cells is expected to be limited by the intratumoral high pressure.

Overall, this data points out the importance of providing an alternative entry pathway to adenoviral vectors for the infectivity of tumors. In all cell lines and tumor types analyzed, a vector that can use the natural entry pathway via primary binding to CAR and an additional entry pathway via binding to integrins transduces more efficiently than a vector that only can use the natural CAR receptor.

EXAMPLE 4

Replication-competent, E1-transcomplementation Vectors

Most replication-defective adenovirus vectors in preclinical and clinical use have deleted E1A and E1B genes [14]. These deletions render the vector unable to replicate, or replication-incompetent, and these vectors can replicate only when E1 proteins are supplied in trans. These replication-incompetent vectors transduce the cells that they infect but they do not produce any progeny.

Figure 10:
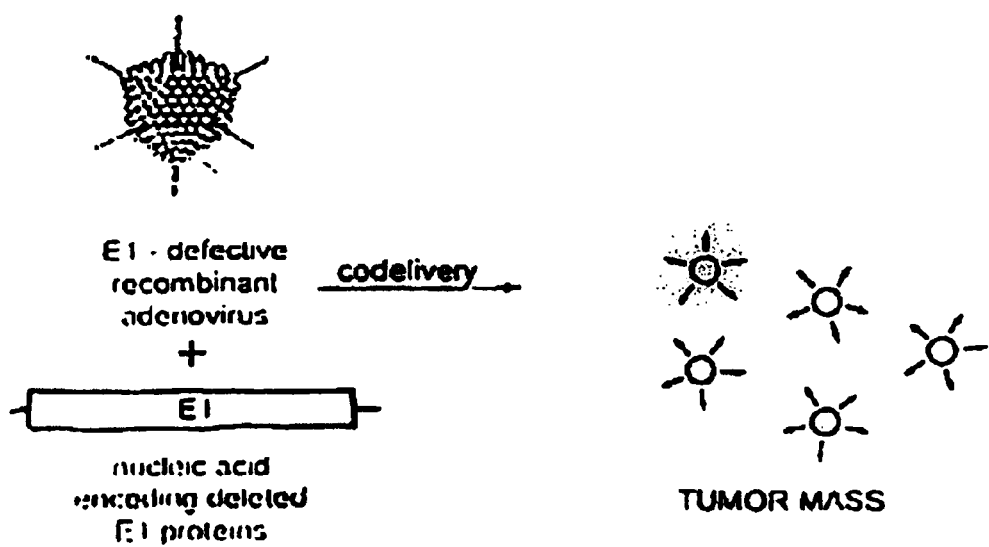
FIG. 10 shows a conceptual representation of the conditional replication enablement system for adenovirus. The initial introduction of recombinant virus into the tumor mass infects the cells shown as circles. The replication enabling plasmid converts these cells in vector-producing cells. The produced vector can infect adjacent cells (arrows).

A conditional replication enablement system for adenovirus has been developed in which the E1 genes are supplied in trans to cells infected with E1-deleted vectors [31,48,49] (FIG. 10). The replication-enabling system has been developed primarily as a means of amplifying transduction in tumor nodules. In order to achieve a more extensive amplification of the vector and lysis of tumor cells, the secondarily produced vector should propagate continuously in tumor cells. Replication-enabling has been achieved by linking plasmids encoding the E1 proteins to the exterior of the capsid [31,44,48] or separately introducing the plasmid using cationic lipids [49]. These experiments provided evidence that replication-enabling systems could achieve amplification of the in vivo therapeutic response of an adenoviral vector carrying HSV-TK [49]. E4-deleted adenoviruses have also been transcomplemented with a plasmid containing the E4 open reading frame 6 gene or the complete E4 region [44]. E4 transcomplementation is important in the context of reducing immunogenicity and increasing long-term gene transfer [14].

In order to further enhance the utility of the replication-enabling system, it is a goal of the present invention to reduce the possibilities of recombination between the E1-deleted vector and the transcomplementing plasmid. This recombination would generate replication-competent adenoviruses (RCA). Therefore, an E1 expressing plasmid has been constructed, pE1FR, in which E1a and E1b sequences are in tandem but oriented in opposite 5' to 3' direction. Cells co-transduced with this plasmid and an E1-defective adenoviral vector using cationic liposomes resulted in replication-defective adenovirus production levels comparable to that achieved by co-transduction of the virus and pE1 (FIG. 11) [49]. Comparable results weve obtained with HeLa, A549 and SKOV3-ip1 cell lines.

Figure 11:
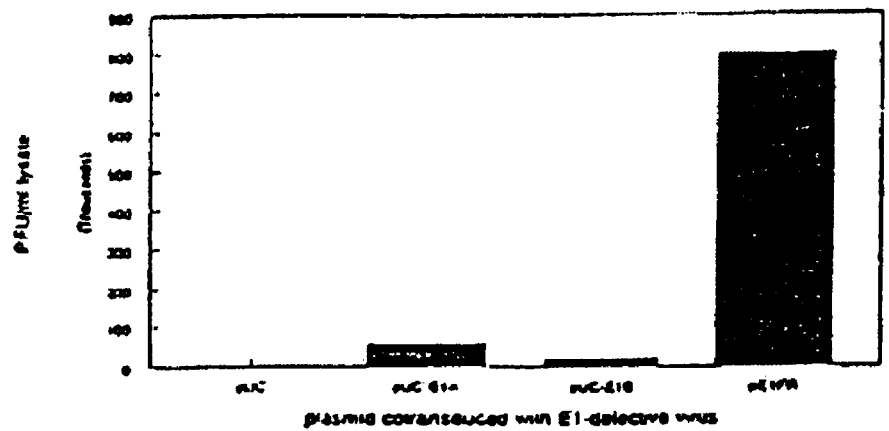
FIG. 11 shows functional analysis of pE1FR. LS174T cells were cotransduced with the plasmid indicated in the abscissa as a liposomic complex (0.5 µg DNA/1.0 µg DOTAP:DOPE) and AdCMVluc (MOI=1). Forty eight hours after transduction, the amount of virus present in the lysate of cells was measured by a plaque assay in 293 cells.
Figure 12:
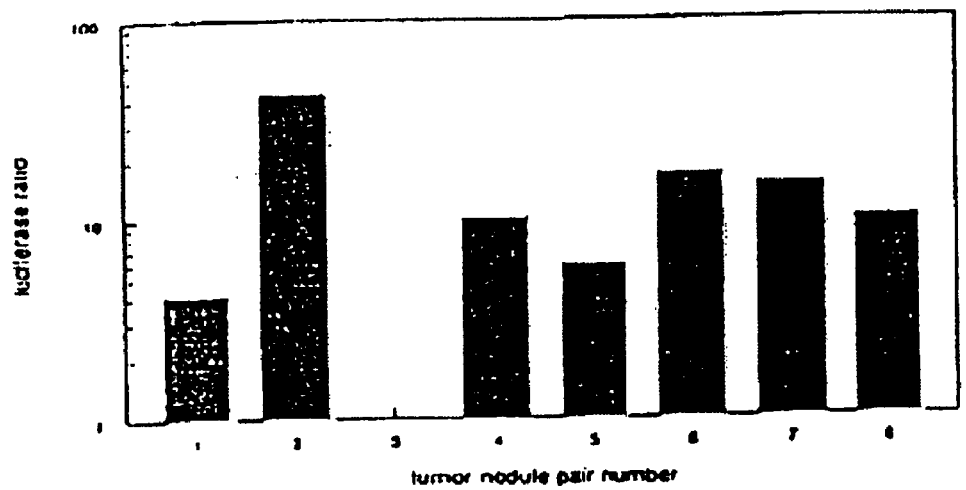
FIG. 12 shows enhancement of E1-defective adenoviral transgene expression by pE1FR administration. Nude mice engrafted with human lung adenocarcinoma tumors (A549 cell line) received an intratumoral injection of E1-defective virus AdCMVluc ($10^8$ pfu per 8–10 mm diameter tumor) mixed with plasmid pE1FR or pUC13 (3 µg). One week later, luciferase expression in tumors was measured. Each bar represents one mouse with a pair of tumors, one treated with AdCMVluc and pE1FR and the other one with AdCMVluc and pUC13. The ratio of luciferase expression in the tumor treated with pE1FR versus the one treated with pUC13 is shown.

This demonstrates that pE1FR can transcomplement E1-deleted vectors and convert the infected cells into vector-producing cells. To demonstrate that this vector could also enhance the tumor transduction achieved with an E1-deleted vector in vivo, tumors were injected with E1-defective virus mixed with pE1FR, or a plasmid control. Assessment of the luciferase content showed that 6 out of 8 tumors had increased luciferase activity in the pE1FR group relative to the controls (FIG. 11).

This data indicates that E1-expression vectors, such as pE1FR, represent a feasible way to increase the in vivo transduction efficiency of E1-deleted vectors in tumors. The amplification of the transduction efficiency achieved with a system such as the replication-enabling system is limited, however, by the inability of the vector progeny to keep replicating. The replication-enabling function needs to be carried over in the vectors produced by the tumor cells to allow repeated cycles of replication.

EXAMPLE 5

Replication Competent Vectors Dependent Upon IL-6

As shown in the data above, the replication-enabling system has been developed primarily as a means of amplifying transduction in tumor nodules. Methods have also been explored to achieve a more extensive amplification of the vector and subsequent lysis of tumor cells. To fulfill this goal, the secondarily produced vector should propagate continuously in tumor cells and incorporate a regulatory mechanism that confines this propagation to the tumor. E1a 12s and 13s adenoviral proteins are necessary to induce the expression of other viral genes, and therefore, an E1a-deleted vector is impaired in its replication [14]. It has been reported that interleukin 6 can induce transcription factors that are able to substitute for the E1a activity of adenovirus [50].

Figure 13:
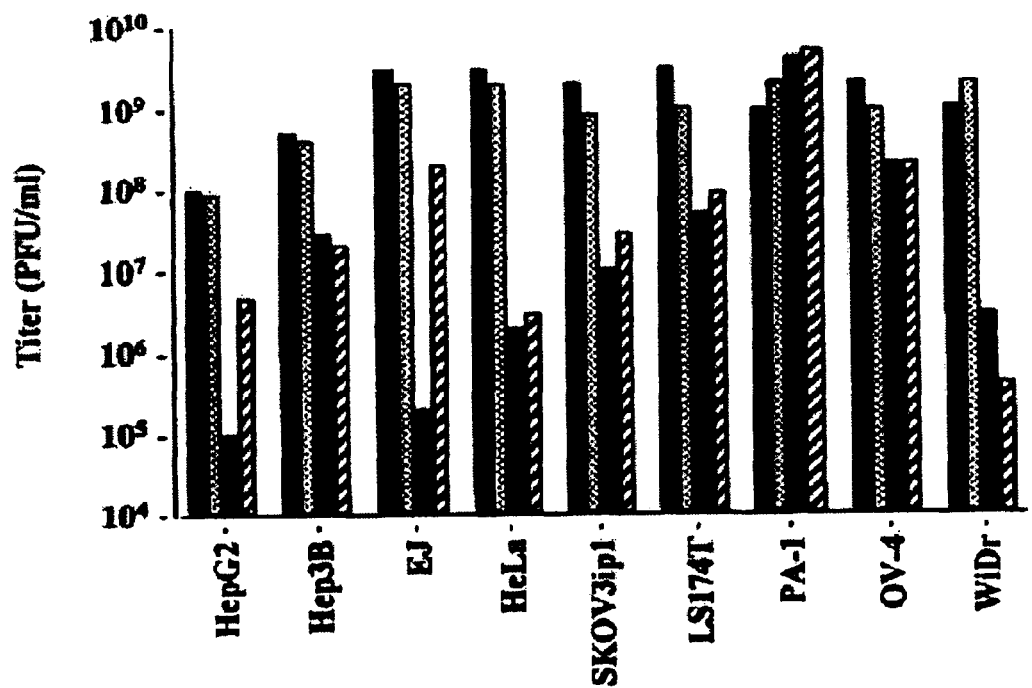
FIG. 13 shows the E1A-like activity of IL-6 can be exploited to produce Ad312 virions in HepG2 cells and in a variety of cell lines responsible to IL-6. Cells (1 to $4 \times 10^5$) were infected with wild type adenovirus or Ad5dl312 at an MOI of 10 in the absence or presence of 100 units/ml of rhIL-6. Six days later, cells were lysed and the amount of virus in the lysates was quantitated by plaque assay in 293 cells. For each cell line, bar from left to right represent wild type, wild type+IL-6, dl312, and dl312+IL-6.

To explore whether an E1a-deleted vector such as Ad5dl312 could replicate in the presence of IL-6 in different cancer cell lines, cells were infected with dl312 in the presence of IL-6 and the progeny were examined (FIG. 13). In all cell lines, infectious virions were produced to a certain extent in the presence and absence of IL-6, although in lower amounts than the wild type adenovirus. The effects of IL-6 in dl312 production were markedly seen in two cell lines: HepG2 and EJ. In HepG2 cells, IL-6 resulted in a 1.5 log increase of viral production.

Figure 14A:
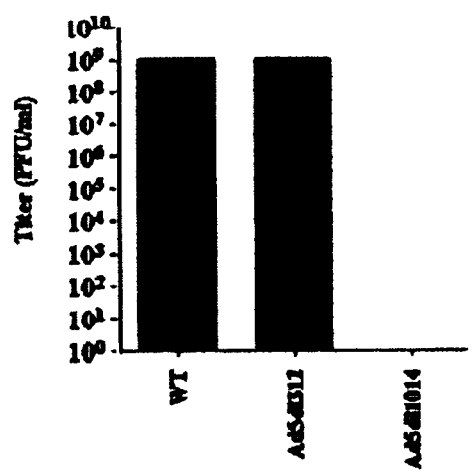
FIG. 14A shows that six days post-infection, cells were lysed and the amount of virus in the lysates was measured by plaque assay in 293 cells (for WT and dl312) or W162 cells (for dl1014).
Figure 14B:
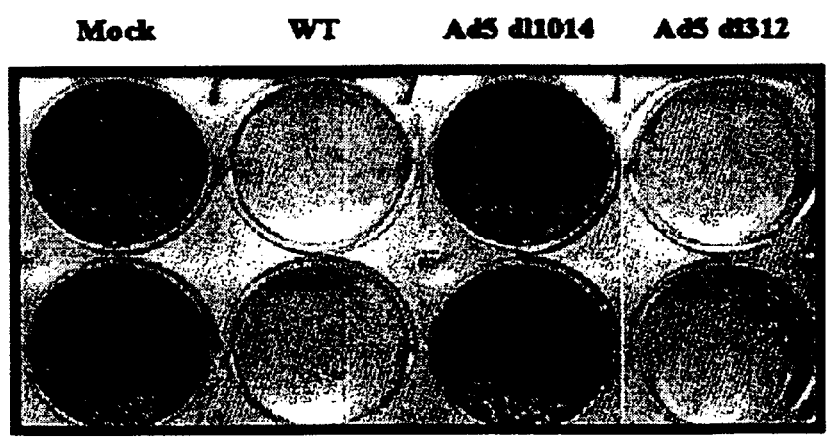
FIG. 14B shows that in a separate experiment, seven days post-infection cells were fixed with formaldehyde and stained with crystal violet. No viable cells were found in wells with cells infected with WT and dl312 viruses in contrast to mock-infected and dl1014-infected cells.
Figure 15:
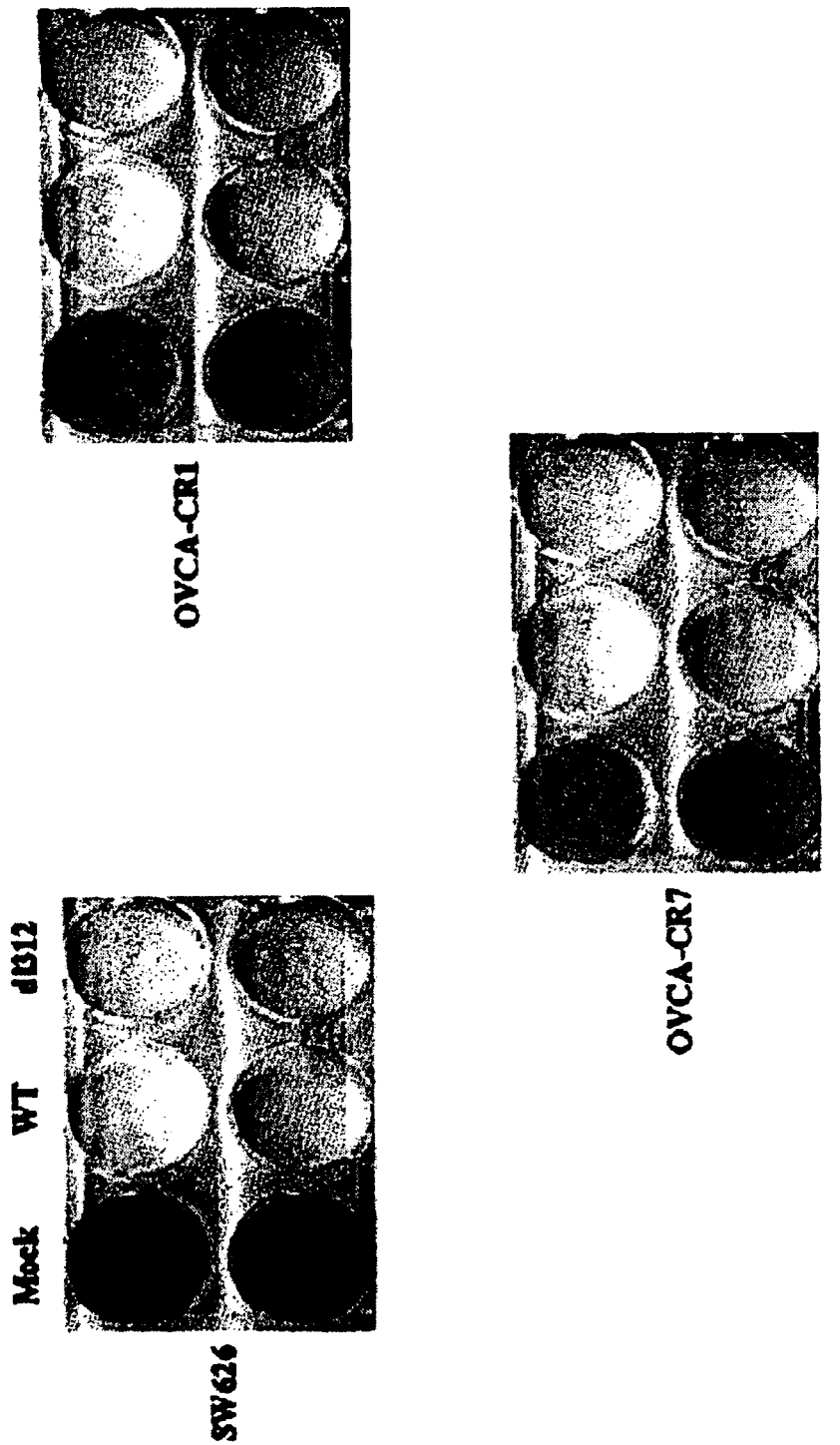
FIG. 15 shows that E1a-deleted virus dl312 can lyse human ovarian cancer cells. SW626 cells and two primary cultures of two ovarian tumors were infected with E1-a deleted Ad5dl312, wild type or E4-deleted Ad5dl1014 (MOI=10). Seven days post-infection, cells were fixed with formaldehyde and stained with crystal violet. No viable cells were found after infection with the wild type and dl312 viruses in contrast to mock-infected and dl1014-infections.

These experiments demonstrate that the IL-6-inducible E1a-like activity can complement the E1a deletion during infection of HepG2 and EJ cells. To overcome the requirement of exogenous IL-6, carcinomas, e.g., cervical, chorio, and ovarian, that have an IL-6 autocrine loop [51–53] were infected with the E1A-deleted virus, dl312. OVCAR-3 and SW626 cells have a functional IL-6 autocrine loop [53]. Upon infection of OVCAR-3 cells with Ad5dl312, or wild type or E4-deleted control viruses, Ad5dl312 was produced to levels similar to levels produced by the wild type control, even in the absence of IL-6 (FIG. 14). This IL-6-independent replication of E1a-deleted virus was also demonstrated in SW626 cells a n d primary cultures of ovarian tumors (FIG. 14).

Figure 16:
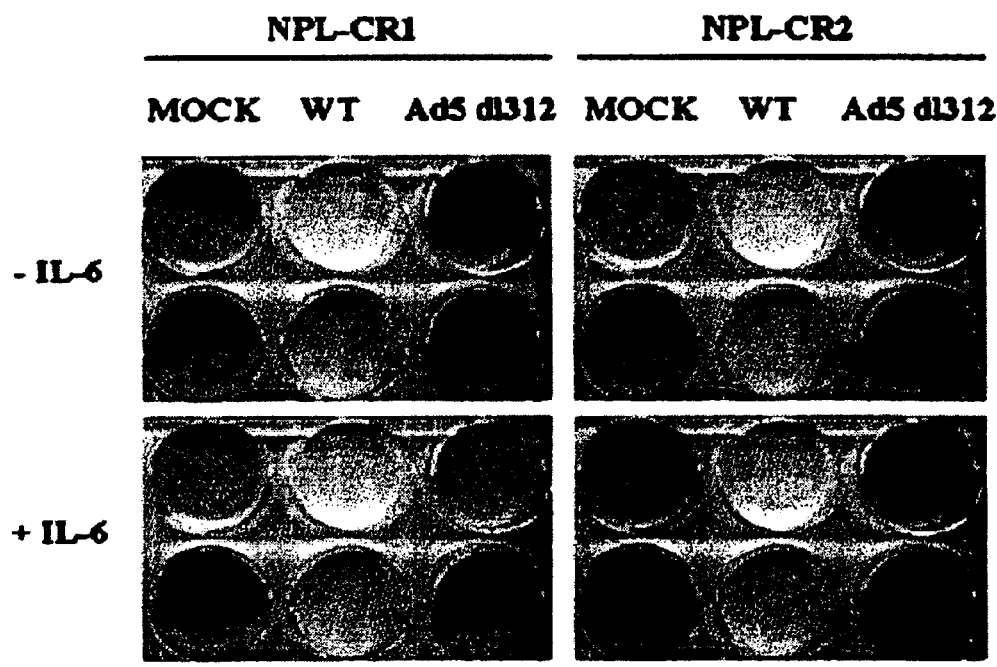
FIG. 16 shows that normal peritoneal lining cells do not support the replication of the E1a-deleted Ad5dl312 adenovirus even in the presence of exogenous IL-6. Human mesothelial were cells isolated from normal peritoneal lining by mechanical disruption and collagenase D treatment. Cells were infected with E1-a deleted Ad5dl312 or wild type control (MOI=10) in the absence or presence of IL-6. Twelve days post-infection cells were fixed with formaldehyde and stained with crystal violet. Cells remained viable when infected with Ad5dl312.

These results indicate that cells with an autocrine loop of IL-6 can selectively support the replication of Ad5dl312 without the addition of exogenous IL-6, and that these cells are lysed by the E1a-deleted virus. The effects of the E1a-deleted virus in normal cells were examined. To test the ability of this virus to propagate in normal cells adjacent to ovarian tumors, human mesothelial cells isolated from peritoneal lining tissue were infected. Contrary to the wildtype virus control, Ad5dl312 did not replicate in these cells even in the presence of IL-6 (FIG. 16).

Overall, this data indicates that E1a-deleted adenovirus can be complemented by the IL-6-induced E1a-like activity found in several tumors. E1a-deleted vectors are, however, limited by the fact that E1a intrinsic activity has been noted in normal cells [54]. IL-6 production, in the other hand, could result from the injection of the vector in an immunocompetent host and this natural inflammatory response would result in nonspecific complementation. Clearly, new mechanisms of tumor-specificity need to be incorporated to control the replication of adenoviral vectors.

SUMMARY

The clinical benefits of cancer gene therapy achieved with non-replicative adenoviral vectors have been hampered by the significant number of cells in a tumor which have been left unaffected by the direct or indirect effects of the transgenes. Conditional replicative adenoviruses may represent a significant improvement to solve this problem, but efficient infectivity and tumor-selective replication need to be achieved to realize their full potential.

The importance of the modification of the adenoviral capsid to increase the binding of the vector to the tumor cells has been demonstrated herein. An integrin-binding RGD motif inserted in the HI loop of the adenoviral fiber confers an additional binding pathway besides the natural coxsackie-adenovirus receptor, and this dramatically increases the infectivity of the vector. The data herein also indicates that transduction efficiency can also be enhanced if the vector is able to replicate in the tumor. A transcomplementation system has been developed as a means to evaluate the effects of replication on the transduction efficiency. This replication-enabling system also provides the opportunity to analyze the efficacy and specificity of different tumor-specific replication mechanisms before incorporating these mechanisms into a single viral vector in a ciscomplementation strategy that will allow continuous replication. In this regard, continuous tumor-selective replication has been shown using E1a-deletion mutants that propagate in tumors due to an E1a-like activity.

EXAMPLE 6

Incorporation of RGD-fiber into Currently Defined Conditional Replicative Mutant Viruses As an initial approach towards comparing the therapeutic potential of an RGD-modified versus an unmodified replicative adenovirus, conditional replicative mutants that have been previously described were chosen. Deletion of the E1b-55K protein was designed to confer selective replication to adenoviruses in cells lacking functional p53 [30]. In a similar way, deletion of the Rb-binding sites of E1a has been proposed to achieve selective replication in cells lacking Rb. These deletion mutants are used as established models of selective replication-competent viruses.

The initial plasmid to construct these deletions is pXC1, which contains adenoviral sequences from basepair 22 to 5790 (Microbix, Hamilton, Canada). For the E1b55K deletion, the region from Sau3A1 (Ad5#2426) to BglII (Ad5#3328) is removed by ligation of the 1 kb XbaI-Sau3A1 DNA fragment with the 7.9 kb Xba1-BglII DNA fragment to yield plasmid pXC-55K-. For an E1a deletion construct that abrogates binding to Rb, a derivative of pXC1 (pXC1 Δ24) is obtained with E1a deleted in residues 122 to 129 (Dr. Juan Fueyo, MDACC). This deletion affects the residues of the conserved region 1 of E1a necessary to bind Rb [55]. These E1b and E1a deletions are incorporated into the viral genome by homologous recombination with plasmid pVK503, containing either an unmodified fiber or an RGD-modified fiber. From the plasmids obtained by homologous recombination, the unmodified 55k- and Δ24 mutants are generated by releasing the viral genome with PacI and transfecting into 293 cells. Viruses are amplified and purified by double CsCl gradient, and titered in 293 cells for in vitro and in vivo experiments. The presence of mutated E1, altered fiber, and contaminating wild type E1, is analyzed by PCR as well as by sequencing of viral DNA isolated from CsCl-purified virions.

Figure 17A:
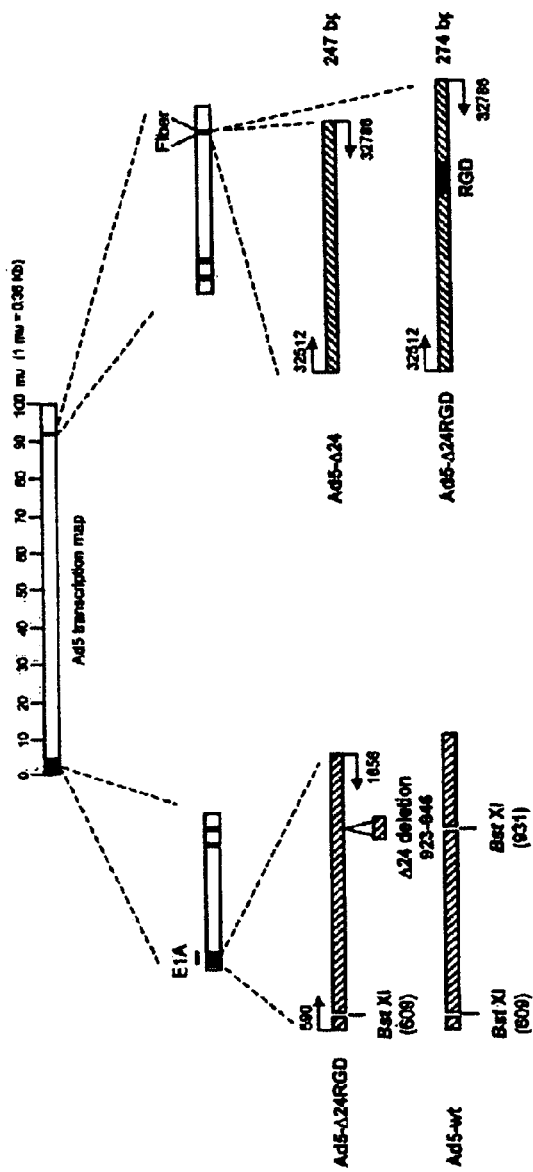
FIG. 17A shows the map of E1A and fiber encoding regions of Ad5-Δ24RGD amplified by PCR, showing the 24-bp deletion and the introduced RGD encoding sequence.
Figure 17B:
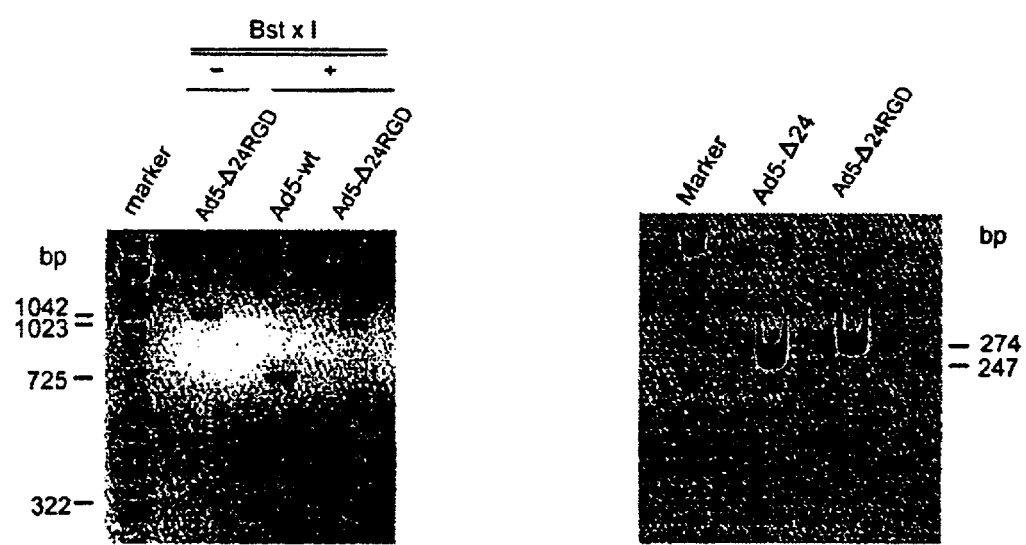
FIG. 17B shows restriction analysis of Ad5-Δ24RGD. The presence of the 24-bp deletion was confirmed by BstX I digestion of the PCR product of the E1A region. The fragments were resolved on a 2% agarose gel, and visualized by UV fluorescence. Marker: Gibco 1 Kb DNA ladder. The presence of uncleaved PCR product verified the presence of the deletion (left). PCR amplification products of the region encoding the fiber from Ad5-Δ24 and Ad5-Δ24RGD were resolved on a 6% acrylamide gel. Marker: Gibco 100 bp DNA ladder. The bigger size (27 bp) of Ad5-Δ24RGD band indicates the presence of the sequence encoding RGD (right).

The 24-bp deletion in the E1A gene and the RGD encoding sequence in the fiber were verified by PCR (FIG. 17). The presence of the RGD motif in the modified fiber was confirmed b PCR employing fiber primers FiberUp (5'-CAAACGCTGTTGGATTTATG-3', SEQ ID NO: 2) and FiberDown (5'-GTGTAAGAGGATGTGGCAAAT-3', SEQ ID NO: 3). The Δ24 deletion was analyzed by PCR with primers E1a-1 (5'-ATTACCGAAGAAATGGCCGC-3', SEQ ID NO: 4) and E1a-2 (5'-CCATTTAACACGCCATGCA-3', SEQ ID NO: 5) followed by BstXI digestion. Of note, no adenoviruses having wild-type E1 or wild-type fiber appeared throughout the propagation of Ad5-Δ24RGD, a finding that confirms the lack of endogenous adenoviral sequences in A549 cells.

EXAMPLE 7

Evaluation of Infectivity of RGD-modified Conditional Replicative Viruses

Procedures described above are used to demonstrate that the RGD-modified 55K- and Δ24 virions bind to integrins. ELISAs are performed with immobilized virions incubated with purified αvβ3 integrins and anti-α subunit monoclonal antibody, VNR139. The modified replicative viruses are examined to determine if they are able to bind cells via a CAR-independent pathway. 293, HUVEC, and RD cells are used, as enhanced RGD-mediated transduction of these cell lines has already been demonstrated. For binding analysis, virions are labeled with $^{125}$I and incubated with cells. Recombinant knob protein is used as an inhibitor to measure CAR-independent binding. Infectivity of modified and unmodified 55K and Δ24 mutants in ovarian, lung and other tumor cell lines, as well as in primary tumors, are compared. These experiments indicate that the RGD-modified viruses infect tumor cells more efficiently than the non-modified vectors.

EXAMPLE 8

Evaluation of Oncolytic Potential of RGD-modified Conditional Replicative Viruses Cell lines A549 human lung adenocarcinoma and LNCaP human prostate cancer cell lines were obtained from the American Type Culture Collection (Manassas, Va.). The cells were cultured in Dulbecco's modified Eagle's medium (DMEM) supplemented with 5% heat-inactivated fetal bovine serum (FBS), 100 I.U./ml penicillin, and 100 μg/ml streptomycin.

Virus DNA Replication A549 cells cultured at 90% confluence in 6-well plates were infected with Ad5-Δ24 or Ad5-Δ24RGD at a dose of 0.01 viral particles/cell. After 2 h, the cells were washed and maintained in DMEM-5% FBS with 1 μCi/ml bromodeoxyuridine (BrdU) (Amersham Pharmacia Biotech Inc., Piscataway, N.J.). Attached and detached cells were harvested at 2, 4, 6, and 8 days after infection, and encapsidated viral DNA was purified by the spermine-HCl method [63]. One third of the total purified viral DNA (corresponding to 6×10$^5$ cells) was digested with HindIII and resolved in 1% agarose gel. The fragments were transferred to a nylon membrane (Amersham Pharmacia Biotech), fixed, blocked in blocking buffer (50 mM Tris-HCl, pH 7.5, 150 mM NaCl, 5% dry milk, 2% Tween 20), and incubated with mouse anti-BrdU IgG (DAKO, Carpinteria, Calif.) at 4° C. overnight. The membrane was washed next day, incubated with peroxidase-labeled anti-mouse antibody (Amersham), and processed by Western blotting analysis with the ECL system (Amersham). The membrane was exposed to Kodak Biomax ML film for 3 seconds at room temperature and developed in an automated processor.

Adenovirus Yield Assay A549 cells cultured at 90% confluence in 6-well plates were infected with 0.01 particles/cell of Ad5lucRGD, Ad5-Δ24, or Ad5-Δ24RGD for 2 h. The cells were then washed thoroughly with PBS to remove all non-adsorbed viruses, and maintained in DMEM-5% FBS. After 8 days, cells and media were harvested, freeze-thawed 3 times, centrifuged, and the titer was determined by plaque assay with A549 cells as targets.

Oncolysis Assay A549 and LNCaP cells cultured in triplicate in 6-well plates were infected with one of the three types of adenovirus at doses of 0.001 or 0.01 viral particles/cell when 90% confluence was reached. Eight or ten days after infection, the cell monolayers were washed with PBS, fixed with 10% fresh buffered formaldehyde for 10 min, and stained with crystal violet solution (1% crystal violet [w/v], 70% ethanol). After 1 h staining, the plates were rinsed with tap water and dried.

In vitro Cytotoxicity Assay (XTT) A549 and LNCaP cells were seeded and infected in parallel with the ones used for the oncolysis assay described above. Eight or ten days after infection, the media was carefully removed, and fresh media containing 200 ug/ml of 2,3-bis[2-methoxy-4-nitro-5-sulfophenyl]-2H-tetrazolium-5-carboxyanilide (XTT) (Sigma, St. Louis, Mo.) was added. Cells were then incubated for 3 h at 37° C. The content of each well was transferred to a microwell plate, and the light absorbance was read at 450 nm in a microplate reader (Molecular Devices Corp., Sunnyvale, Calif.). The number of living cells was calculated from non infected cells cultured and treated with XTT in the same way as were the experimental groups.

Subcutaneous tumor xenograft model in nude mice Female athymic nu/nu mice (Frederick Cancer Research, Md.) 8–10 weeks old were used to grow A549 s.c. nodules. Eight million cells were xenografted under the skin of each flank in anesthetized mice. When the nodules reached 60–100 mm$^3$, a single dose of $10^9$ viral particles (high-dose experiment, n=5) or $10^7$ viral particles (low-dose experiment, n=4) of Ad5lucRGD, Ad5-Δ24, Ad5-Δ24RGD, Ad5-wt or PBS was administered intratumorally (i.t.). Tumor size was monitored twice a week, and fractional volume was calculated from the formula: (length×width× depth)×1/2. The mice were euthanized 35 days after the treatment because of the size of the tumors in the control group. Statistical differences among groups were assessed with student's t tests.

Adenovirus Hexon Immunodetection The presence of adenovirus hexon in the treated tumor xenografts was assessed by immunofluorescence at the end of the experiment. Frozen A549 nodule specimens were sections, fixed in 3% formaldehyde, and blocked with normal donkey serum for 30 min at room temperature. Then goat anti-hexon antibody (Chemicon Inc., Temecula, Calif.) was applied for 2 h at room temperature, followed by PBS rinse and incubation with Alexa Fluor 488-labeled donkey anti-goat antibody (Molecular Probes, Eugene, Oreg.) for 30 min at room temperature. The slides were then rinsed and counterstained with Hoechst 33342 (Molecular Probe) for 10 min, and analyzed under a fluorescent microscope (Leitz Orthoplan).

Figure 18:
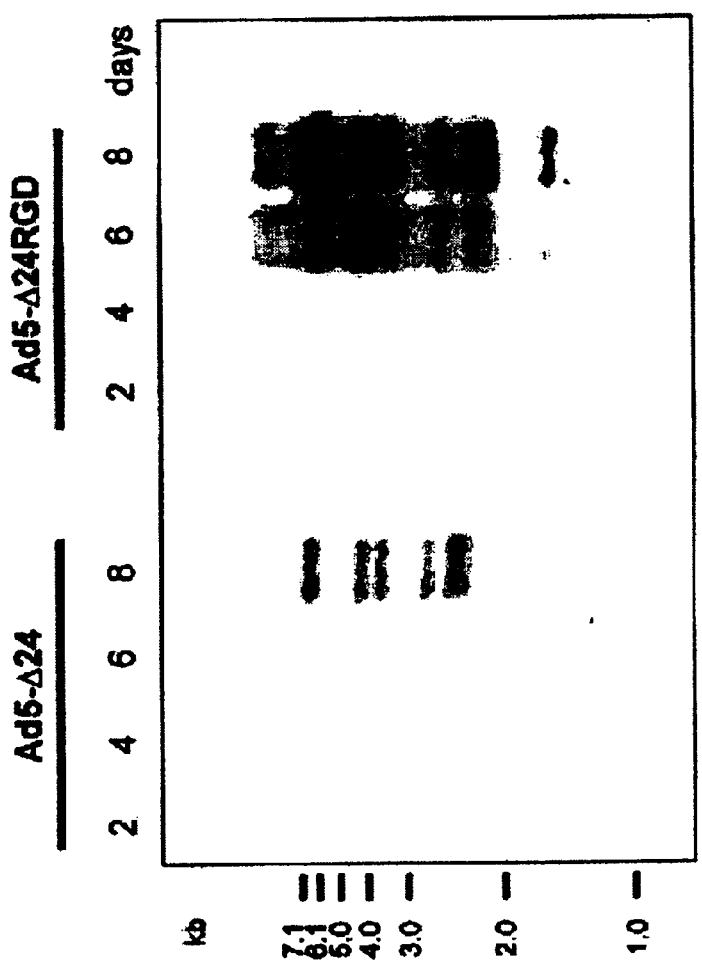
FIG. 18 shows propagation efficiency of Ad5-Δ24 versus Ad5-Δ24RGD. A549 cells were infected with 0.01 particles/cell of Ad5-Δ24 or Ad5-Δ24RGD and incubated in medium containing 1 μCi/ml of BrdU. At the indicated times after infection, the cells were harvested, and the encapsidated DNA was purified by the spermine-HCl method. Viral DNA from $6 \times 10^5$ infected cells was digested with HindIII, electrophoresed, and the resulting fragments were blotted into a membrane that was processed with a mouse anti-BrdU antibody. The amount of BrdU incorporated into viral DNA indicated that Ad5-Δ24RGD propagation is more efficient than that of Ad5-Δ24.

Results After structural confirmation, the replication capacity of Ad5-Δ24RGD and Ad5Δ24 were compared in A549 cells. Cell monolayers were infected with low dose of each virus (0.01 viral particles/cell), and were maintained in media with BrdU throughout the 8-day incubation period. The encapsidated viral DNA was purified on days 2, 4, 6, and 8 postinfection. Viral DNA corresponding to 6×10$^5$ cells was analyzed by Southwestern blot using anti-BrdU antibody. As indicated by the BrdU incorporated into replicating viral DNA, Ad5-Δ24RGD propagation was more efficient than that of Ad5-Δ24 (FIG. 18). The Ad5-Δ24RGD DNA can be detected not only sooner (day 6) compared to Ad5-Δ24 DNA (day 8), but in greater amounts. Thus, the infectivity advantage conferred by RGD incorporation into the fiber knob increased adenovirus propagation in target cells. As this tropism modification would not be anticipated to alter fundamental aspects of the viral replication cycle, this effect was likely achieved exclusively on the basis of the infectivity enhancement allowed by routing the virus through CAR-independent pathways.

Based on the previous experiment, the actual amount of infectious virus produced by Ad5lucRGD, Ad5-Δ24, or Ad5-Δ24RGD in A549 cells at 8 days after infection were quantified by plaque assay. Ad5-Δ24RGD produced a viral yield of 3.75×10$^9$ pfu/ml, which was 43 times higher than that of its unmodified Ad5-Δ24 counterpart (8.75×10$^7$ pfu/ml). No virus was obtained from the nonreplicative control Ad5lucRGD infected cells. These results are consistent with the fact that modifying the fiber knob with an RGD motif led to enhancement of viral infectivity and an increase in the production of infectious adenovirus.

Figure 19A:
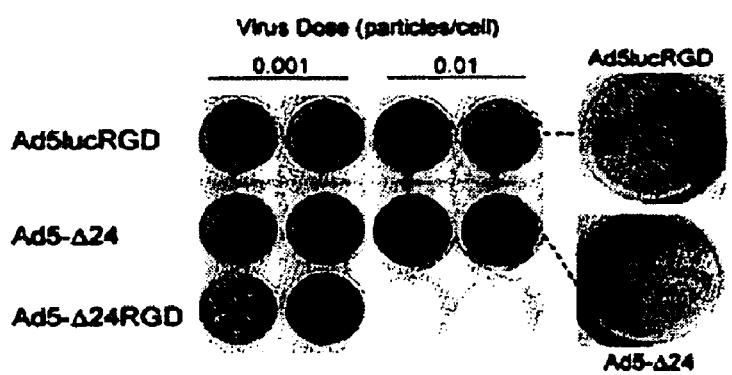
FIG. 19A shows A549 and LNCaP cells infected with 0.001 or 0.01 particles/cell of Ad5lucRGD, Ad5-Δ24, or Ad5-Δ24RGD. Eight (A549) and 10 days (LNCaP) later, the cells were fixed and stained with crystal violet. A higher magnification of two wells is presented to show the incipient cytopathic effect of Ad5-Δ24.
Figure 19A:
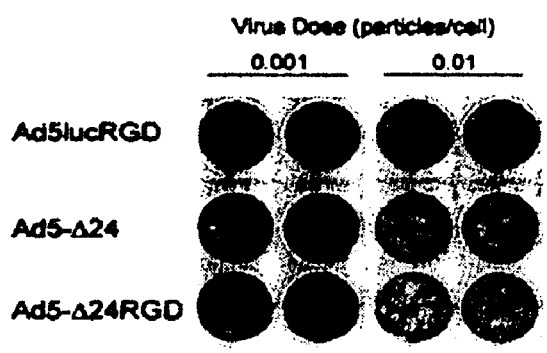
Figure 19B:
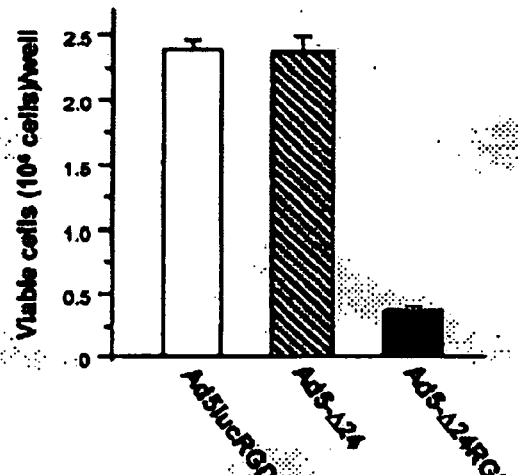
FIG. 19B shows cell viability analyzed with an XTT colorimetric assay. In both cell lines, Ad5-Δ24RGD had higher lytic potency than did its unmodified counterpart, as shown by the percentage of viable cells remaining in the corresponding treatment conditions.
Figure 19B:
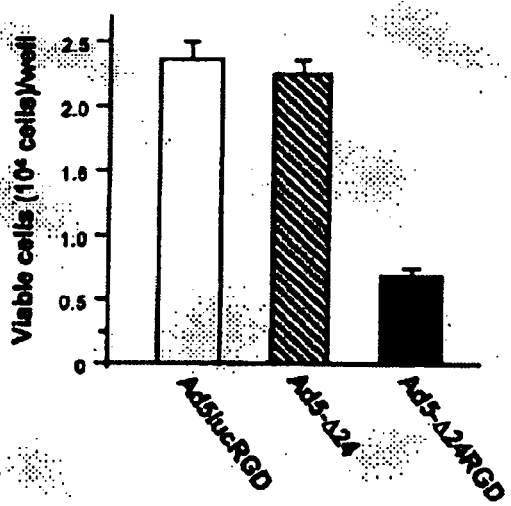

To demonstrate the increased lytic potency of Ad5-Δ24RGD, A549 and LNCaP cells were infected with small amounts of each virus to allow multiple cycles of viral replication over the ensuing 8 days, then stained the attached cells with crystal violet and counted viable cells by XTT assay. In both cell lines, the fewest viable cells were detected in the Ad5-Δ24RGD-infected group (FIGS. 19A and B). The cell lysis capacity of Ad5-Δ24RGD is 7 times higher in A549, and 3.5 times higher in LNCaP compared to Ad5-Δ24. These results demonstrate that the fiber knob modification enhanced adenoviral lytic potency over that of the Ad5-Δ24 virus.

Figure 20A:
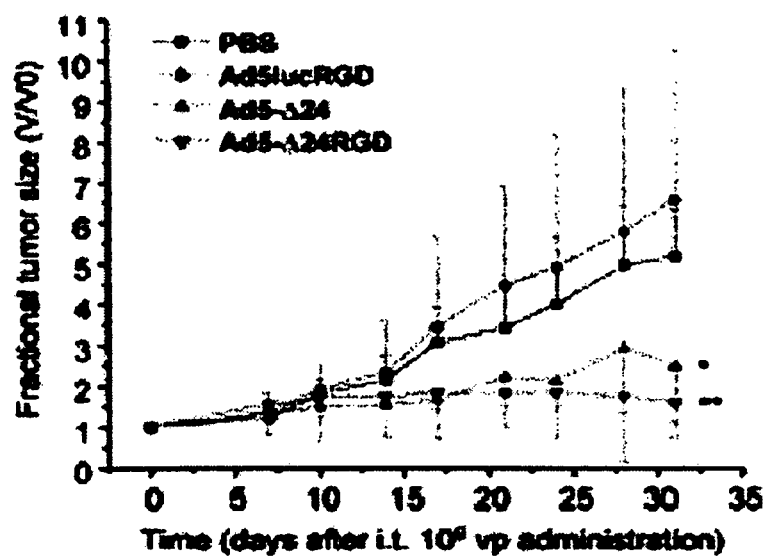
FIG. 20A shows subcutaneous A549 xenografts in nude mice treated with a single i.t. injection of $10^9$ viral particles of Ad5lucRGD, Ad5-Δ24, Ad5-Δ24RGD, or with PBS alone.
Figure 20B:
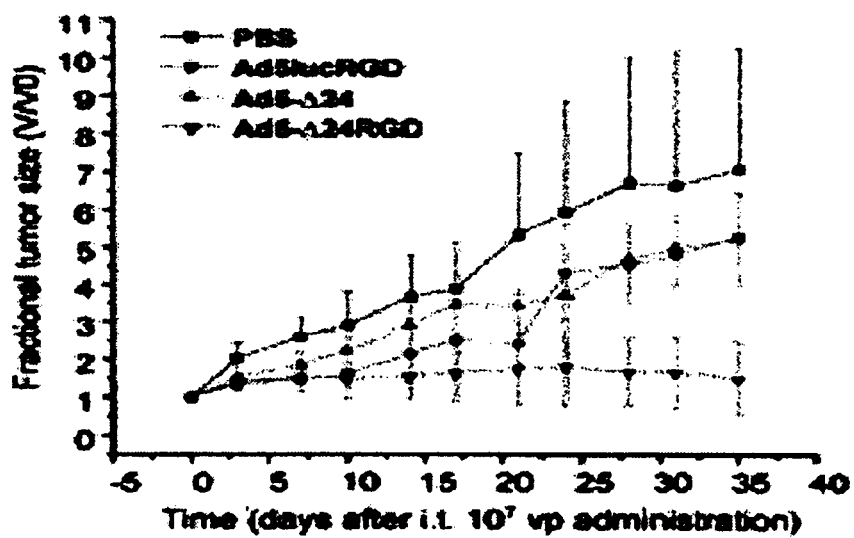
FIG. 20B shows subcutaneous A549 xenografts in nude mice treated with a single i.t. injection of $10^7$ viral particles of Ad5lucRGD, Ad5-Δ24, Ad5-Δ24RGD, or with PBS alone. Tumor size was measured twice a week. Results are shown as fractional tumor volumes (V/V0, where V=volume at each time point; V0=volume at adenovirus injection), and each line represents the mean of 5 tumors (±SD) in the high-dose group, and 4 tumors (±SD) in the low-dose group. In the high-dose experiment, both CRAds show a similar oncolytic effect that results in smaller tumors compared to PBS treated groups (*Ad5-Δ24 p<0.05; **Ad5-Δ24RGD p<0.01). However, in the low-dose experiment, tumors treated with Ad5-Δ24 followed a growth curve similar to that of tumors treated with non-replicative Ad5-lucRGD; tumors treated with Ad5-Δ24RGD did not grow (p<0.01 compared to PBS).
Figure 20C:
FIG. 20C shows the detection of adenovirus hexon in tumor xenografts by immunofluorescence. Frozen sections of tumor specimens injected with (a) Ad5lucRGD, (b) Ad5-Δ24, and (c) Ad5-Δ24RGD were treated with goat anti-hexon antibody and Alexa Fluor 488-labeled donkey anti-goat antibody, and nuclei were counterstained with Hoechst 33342. Images were captured from Leitz fluorescence microscope (100× magnification) with a double filter. Sections taken from tumors treated with CRAds were positive for adenovirus presence (green dots in b and c), being Ad5-Δ24RGD signal stronger than that of Ad5-Δ24. Samples taken from tumors treated with PBS (not shown) or Ad5lucRGD exhibited no hexon signal (a). i.t., intratumoral; vp, viral particles; Ad, adenovirus.

A goal of this study was to support the oncolytic superiority of infectivity enhanced conditionally replicative adenovirus (CRAd) over that of unmodified adenoviruses in vivo. Since low doses of virus allow several cycles of replication along with destruction of tumor cells, even a single dose would produce a n exponential rise in the number of killed cells, which would extend to the entire tumor. In order to demonstrate this hypothesis, A549 xenografts in nude mice were treated with a single i.t. injection ($10^9$ viral particles) of one of the three viruses or with PBS. At 32 days after injection, both CRAds demonstrated to have an oncolytic effect in the tumors opposite to those treated with nonreplicative virus or with PBS (Ad5-Δ24, p<0.05; Ad5-Δ24RGD, p<0.01 compared to PBS group) (FIG. 20A). Given these results, another experiment was performed in which a 100-fold lower dose ($10^7$ viral particles) of the viruses were administered. This low-dose treatment demonstrated that the oncolytic effect of Ad5-Δ24RGD was superior to that of Ad5-Δ24 (p<0.05). These differences observed between high-dose and low-dose experiments suggest that a threshold dose over $10^7$ viral particles of Ad5-Δ24 is required to obtain an oncolytic effect in tumor nodules (FIG. 20B). To confirm that the CRAds were present in the tumor tissue, immunofluorescence assays were used to detect the virus hexon in tumor samples collected after the low-dose experiment (35 days postinjection). Ad5-Δ24RGD was present in the tumor nodules, as was Ad5-Δ24 to a lesser extent. PBS and Ad5lucRGD treated nodules showed no hexon signal (FIG. 20C). These results corroborate that the partial reduction of tumor mass was due to virus replication and that the RGD modification of the fiber knob conferred infectivity and oncolysis advantage to a CRAd in vivo.

Figure 21:
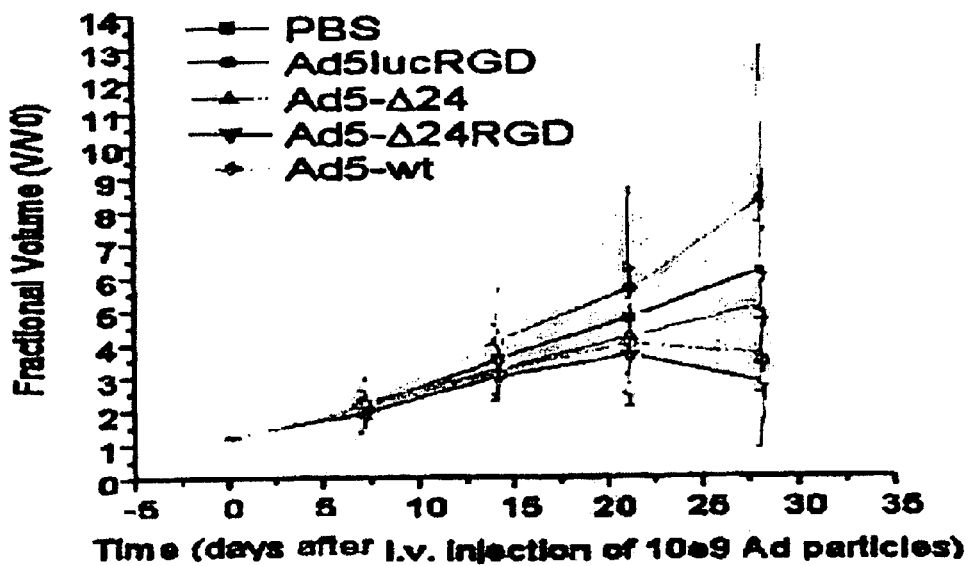
FIG. 21 shows in vivo oncolysis by systemic delivery of infectivity-enhanced CRAds. A total dose of $10^9$ viral particles divided into two consecutive doses of $5 \times 10^8$/day of either Ad5lucRGD, Ad5-Δ24, Ad5-Δ24RGD, Ad5-wt, or PBS were injected in the tail vein of nude mice bearing s.c. A549 xenografts. Tumor size was measured weekly. Results are shown as fractional tumor volumes (V/V0, where V=volume at each time point; V0=volume a t adenovirus injection), and each line represents the mean of 4 tumors (±SD). The data show that modification of the fiber to broaden the tropism of a replicative adenovirus improves the oncolytic potential in a systemic delivery context.

Enhanced oncolytic potential was also demonstrated in a systemic context. A total dose of $10^9$ viral particles divided into two consecutive doses of 5×10$^8$/day of either Ad5lucRGD, Ad5-Δ24, Ad5-Δ24RGD, Ad5-wt, or PBS were injected in the tail vein of nude mice bearing s.c. A549 xenografts. FIG. 21 shows that modification of the fiber to broaden the tropism of a replicative adenovirus improves the oncolytic potential in a systemic delivery context.

Discussion Conditionally replicative adenoviruses (CRAds) are novel and promising agents for cancer therapy. However, their efficacy is predicated upon efficient tumor infection, specific replication, and lateral spread. The deficiency of coxsackie-adenovirus receptor (CAR) in a variety of tumor targets is a limitation to adenovirus infection. In a previous report, it was demonstrated that the insertion of an RGD motif into the HI loop of the fiber knob of non-replicative adenoviruses enhances tumor infection [23, 64], indicating that CAR-independent entry represent a viable way to circumvent CAR deficiency in some tumor types.

In this report, it was demonstrated that the genetic introduction of an RGD sequence in the fiber of a CRAd allows CAR-independent infection that leads to the enhancement of viral propagation and oncolytic effect in vitro and in vivo. The increased initial virus entry into the cells rendered by the RGD-modification results in sooner detection and augmented yields of encapsidated DNA of Ad5-Δ24RGD compared to the unmodified Ad5-Δ24 (FIG. 18). As this tropism modification is not anticipated to alter fundamental aspects of the viral replication cycle, this effect was likely due to the infectivity enhancement allowed by delivering the virus through CAR-independent pathways. Subsequently, studies of the oncolytic potency of CRAds in two cell lines conclude that Ad5-Δ24RGD potency is higher than that of the unmodified virus. Although the XTT assay was not sensitive enough to demonstrate the lytic effect of Ad5-Δ24 compared to the non-replicative Ad5lucRGD, the crystal violet showed early comet-like cytopathic areas in Ad5-Δ24-treated A549 and LNCaP cells, indicating the presence of an incipient lytic effect, whereas Ad5lucRGD treated cells were intact (FIG. 19A). The less notable difference between Ad5-Δ24RGD and Ad5-Δ24 seen in LNCaP cells is explained by the absence of the $\alpha_v\beta_3$ integrins [66], compensated by the presence of other types of RGD-binding integrins ($\alpha_3\beta_1$ and $\alpha_5\beta_1$) [67] that were rapidly saturated (FIG. 19).

Another object of the present invention was to demonstrate the superior oncolytic effect of Ad5-Δ24RGD in an in vivo model. To this end, A549 cells xenografted in nude mice were treated with single, high dose ($10^9$ viral particles) i.t. injections of Ad5lucRGD, Ad5-Δ24, Ad5-Δ24RGD, or PBS, and the results showed that both CRAds (modified and unmodified) yielded similar oncolysis (FIG. 20A). However, when a 100-fold lower dose ($10^7$ viral particles) was administered, it became clear that the oncolytic effect of Ad5-Δ24RGD was higher than that of Ad5-Δ24 ($p<0.05$) (FIG. 20B). Furthermore, the observed oncolytic effects were correlated with the presence of virus progeny in the tumor samples by immunofluorescent detection of adenoviral hexon. Hexon was not detected in PBS (not shown) and Ad5lucRGD treated nodules (FIG. 20C, a), whereas it was detected throughout the tumors treated with CRAds. The comparison between the two CRAds showed that fluorescence in Ad5-Δ24RGD treated tumors was stronger than the one observed in Ad5-Δ24 treated tumors (FIG. 20C, b and c). The lack of fluorescent staining in tumors treated with the non-replicative control Ad5lucRGD indicates that the detected hexon belongs to the viral progeny of Ad5-Δ24 and Ad5-Δ24RGD, and not to the initial inoculum. As regards to the high divergence of the volumes of PBS and Ad5lucRGD treated tumors, factors such as highly heterogeneous cell replication rates and hypoxic and necrotic areas are known to affect individual tumor volume after a critical size is reached. These differences have been noted before when using oncolytic viruses [68,69]. Nevertheless, total resolution of the tumors in the s.c. xenograft model was seen only in some nodules treated with Ad5-Δ24RGD, indicating that administration volume and schema adjustments, such as the ones suggested recently by Heise and co-workers [70], might be necessary to achieve complete oncolysis.

As presented here and elsewhere [71], the efficacy of replication-competent viruses employed as oncolytic agents can be improved at the level of infectivity. As other tumor-binding peptides are isolated [71,72], modifications in addition to the RGD insertion can be considered as well. Of note, the RGD-modification described here does not preclude the binding of the fiber to CAR, and the modified virus can enter the cells through $\alpha_V$ integrins and CAR. One approach to improve specific tumor infection/transduction would be the combination of CAR-ablation and tumor-specific ligands to redirect the virus tropism. Recently, the adenovirus fiber amino acids crucial for CAR-binding abrogation and new tumor-selective peptides have been defined [46, 72, 73]. This combination will generate truly targeted viruses, and the efficiency of their propagation will depend on the amount of the targeted receptor in the same way as the propagation of the unmodified virus depends on CAR. This strategy could be very valuable when the population to be targeted is homogeneous, such as endothelial cells of tumor vasculature.

Other aspects of adenovirus biology that can be improved are replication specificity, tumor cell killing, and evasion from host immune responses. Tumor selectivity has been the major area of research with the design of CRAds based on deletions of adenoviral early genes and utilization of tumor-specific promoters [74, 75]. With regard to cell killing capacity, the combination of oncolysis with suicide genes such as cytosine deaminase and herpes simplex virus thymidine kinase has demonstrated to be superior to either treatment alone [76–78]. In a similar way, the combination of oncolysis with radiotherapy and chemotherapy has also proved to have better efficacy [78, 79]. Immune responses will play an important role in the ultimate outcome of oncolytic virotherapy, an ideal scenario would favor a response that can destroy tumor cells, and yet allow viral spread. The manipulation of the immune response against adenovirus towards a Th1 type could lead in this direction [80]. The use of immunocompetent animals will be needed for the study of immune response to adenovirus, and also ovine and canine adenovirus could be useful for this purpose [81, 82].

Specifically targeted CRAds have theoretical attributes that could make them effective via systemic administration: low toxicity due to lack of adsorption and replication in normal cells and low effective dose due to their amplification. Whether these agents have enough targeting/amplification potency to be efficacious through systemic administration remains to be shown. To ascertain this question, the oncolytic efficiency of enhanced infectivity CRAds administered via tail vein in mice would be determined. It seems that not only the presence of CAR and αv integrin are important for adenovirus infection, but anatomical and immunological barriers are also crucial when considering this route of administration [83]. in particular, vector clearance by liver macrophages is a major obstacle that has to be overcome. This can be attempted with targeting or other strategies that change the physico-chemical properties of the virion such as PEGylation [84]. The emerging picture is that of a targeted adenovirus that remains in circulation for a sufficient period to achieve specific recognition of the target. In such a scenario, the infectivity enhancement maneuvers described herein will clearly improve the therapeutic gain achievable via CRAds.

EXAMPLE 9

Targeting Endogenous Receptors with Chimeric Replication-competent Adenovirus Vectors Squamous cell carcinoma of the head and neck (SCCHN) expresses relatively low levels of the primary adenovirus type 5 (Ad5) receptor, coxsackie-adenovirus receptor (CAR) [64, 85]. This relative deficiency of CAR has predicated the development of CAR-independent transduction strategies to make adenovirus-mediated cancer gene therapy more efficient for this disease. CAR-independent transduction strategies have been made by a number of methods including the development of adenovirus vectors containing chimeric knob domains that alter the virus' target cell tropism [86, 87]. Recently it has been suggested that the receptor for adenovirus type 3 (Ad3) is more highly expressed in SCCHN compared to the Ad5 receptor [88], thereby making the Ad3 receptor as excellent alternative target for SCCHN. Therefore, it is hypothesized that a chimeric Ad5 vector containing Ad3 knob domains would have preferential targeting to SCCHN compared to an Ad5 vector containing only Ad5 knob domain.

Figure 22:
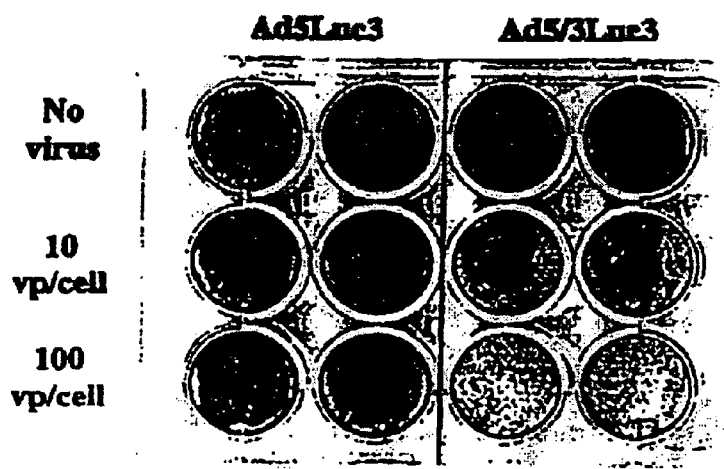
FIG. 22 shows increased oncolytic effect of an Ad3 knob-containing chimeric adenovirus. SCCHN cells were mock-infected or infected with vector particles (vp; 10 vp/cell or 100 vp/cell) of two oncolytic vectors, Ad5Luc3 or Ad5/3Luc3. Three days later the monolayers were stained with crystal violet to estimate the amount of survival tumor cells.

SCCHN cells were infected with equal amount of two oncolytic Ad5 vectors, Ad5Luc3 or Ad5/3Luc3. Ad5Luc3 contains an Ad5 knob domain that necessitates CAR-dependent transduction. Alternatively, Ad5/3Luc3 contains an Ad3 knob domain that utilizes a CAR-independent pathway. The apparent disproportion of Ad5 receptors and Ad3 receptors on this tumor type resulted in more efficient infection and replication of Ad5/3Luc3 compared to Ad5Luc3. As shown in FIG. 22, the ability of Ad5/3Luc3 to more efficiently infect and replicate resulted in a dramatic increase in the oncolytic effect of this virus. Thus, infectivity-enhancement via knob chimerism also improves the oncolytic potency of the CRAd therapy.

EXAMPLE 10

Evaluation of Tumor-selective E2 and E4 Functions

One goal of the present invention was to demonstrate that tumor-selective regulation of E4 and E2 can confer tumor-selective replication to adenovirus. It has previously been shown that E4-deleted adenoviruses can be transcomplemented by conjugating an E4 expression plasmid into their capsid [44]. In this regard, plasmids such as pCEP-ORF6, that contain the E4 ORF6 under a constitutive promoter, can be used to transcomplement E4 deleted viruses, such as dl1014. In order to achieve tumor-selective expression of E4-ORF6, tumor-specific promoters are substituted for the CMV promoter. Among several tumor or tissue selective promoters that have been used in restricting expression of genes to tumor cells, the promoter of the prostate specific antigen (PSA) is used initially. PSA is expressed in prostate cells and has been used to direct expression of TK to prostate tumors [56]. This promoter was chosen to control E4 and E2 in the context of replicative adenoviruses because it has already been used to control E1 in this context (obtained from Dr. Chris Baigma [57]). The promoter is subcloned in front of the E4ORF6 in plasmid pCEPORF6 to obtain a pPSA-ORF6 expression plasmid. To evaluate the conditional replicative phenotype of a PSA-ORF6-regulated virus, this plasmid is conjugated with the E4-deleted virus, dl1014. Conjugates with pCEP-ORF6 or irrelevant plasmids are used as positive and negative controls, respectively. These Ad5dl1014 adenovirus-polylysine-plasmid conjugates are used to infect tumor cell lines that express prostate specific antigen, such as LNCaP, and cell lines that do not express prostate specific antigen, such as DU145 or PC3. In time course experiments, viral replication is measured at the DNA level by Southern blot. The amount of virus produced from the molecular conjugates is measured by plaque assays in W162 cells [44]. dl1014 DNA replication and virus production is observed in all cell lines when using pCEP-ORF6, but only in the PSA-expressing cell line, LNCaP, when using pPSA-ORF6.

These results indicate whether the E4 can be used to control the replication of E4-deleted adenoviruses and whether the PSA promoter restricts this replication to cells expressing PSA. As a reference background and for comparison purposes, a PSA-E1 plasmid is constructed as a derivative of the E1 constructs used in the replication-enabling system, such as pE1FR. An E1-deleted vector and 293 cells are used to evaluate the selective replication conditional to the expression of prostate specific antigen. The differential propagation and the levels of virus production obtained with PSA-E4 and PSA-E1 regulation indicates which of these regulatory mechanism renders better selectivity of replication when used independently.

A similar strategy is followed to achieve selective expression of E2. E2-expression plasmids transcomplement E2-defective viruses using the replication-enabling system. The function of the three open reading frames of E2 (DNA binding protein, terminal protein, and polymerase) are subcloned into separate plasmids. These open reading frames of E2 are then placed under the regulation of the PSA promoter. Appropriate E2-defective mutant viruses, such as Ad5ts125 which contains a temperature-sensitive mutation of E2-DBP, are used to construct the corresponding adenovirus-polylysine-DNA conjugates. As above, these conjugates are used to infect LNCaP, DU145 and PC3 cell lines. Viral DNA replication is measured by Southern blot. Cell lines expressing E2 are used to measure the amount of E2-deleted viruses produced by plaque assays [58].

EXAMPLE 11

Construction of RGD-fiber Adenoviruses with Tumor-selective E4 or E2 Transcriptional Units It is a goal of the present invention to combine the fiber modification with the replication-regulatory mechanisms. Towards this direction, the E4 and/or E2 construct(s) that demonstrated conditional regulation in the replication-enabling system replace the endogenous viral E4 and/or E2 transcriptional unit. For this, the region that is to be modified is subcloned into a small plasmid to facilitate its manipulation. This region is then removed from the plasmid and co-transformed into competent bacteria with a plasmid containing the complete viral genome. The recombination between the viral sequences flanking the modified region and the homologous sequences in the larger plasmid results in the incorporation of the modified region into the adenoviral genome. Before the co-transformation step, it is necessary to cut the large plasmid in a unique site located in the middle of the homology region to avoid the presence of colonies derived from the large plasmid. As there are no available unique sites in the E4 or E2 promoter region, the RecA-assisted cleavage method will be used to restrict in the proper site [59].

This method involves three steps: first, an oligonucleotide spanning the site to be cut in the E2 or E4 promoter region is annealed to the large plasmid in the presence of RecA protein (New England Biolabs, Beverly, Mass.) to form a three-stranded segment. Second, a methylase recognizing this site is then used to methylate all the sites in the large plasmid except the one protected by the oligonucleotide. Finally, the oligonucleotide is removed by heat and the corresponding restriction endonuclease is used to cut the unique non-methylated site. Common site-specific methylases, such as AluI, HaeIII, HhaI, HpaII, etc, and the corresponding restriction endonucleases are purchased from New England Biolabs. Plasmids containing the wild type fiber and plasmids with the modified RGD fiber are used. After the homologous recombination step, the larger plasmids containing the viral genomes with the substituted E4 or E2 regions are cut with PacI to release the viral genome.

Finally, the viruses are obtained by transfection into E4 or E2 complementing cell lines. Viruses are amplified and purified by double CsCl gradient, and titered in these cell lines for in vitro and in vivo experiments. The presence of the E4 or E2 transcription unit regulated with the tumor-specific promoter and of the mutated fiber is analyzed by PCR as well as by sequencing of viral DNA isolated from CsCl-purified virions.

EXAMPLE 12

Localized Models

Subcutaneous tumor nodules are established using the LNCaP and DU145 cell lines. Cells ($10^7$) are mixed 1:1 with Matrigel (Collaborative Bioproducts), loaded into syringes and injected subcutaneously in a total volume of 200 µl into the front flanks of athymic nude mice ($2 \times 10^6$ cells per engraftment site). Initially, three pairs of viruses are compared: PSAE4-RGD versus PSAE4; PSA-E2 versus RGD-PSAE2; and PSA-E1 versus RGD-PSAE1. In a second phase, viruses with double E1/E4 or E1/E2 controlled transcriptional units are also analyzed. Tumor nodules are injected with the appropriate adenovirus or vehicle control (PBS/10% glycerol) when their volume (length×width $2 \times \frac{1}{2}$) reaches $0.2$ cm$^3$. Injections are with a Hamilton syringe in a volume of 20 µl ($\frac{1}{10}$ of tumor volume). The amount of virus injected per tumor is adjusted from $10^4$ pfus (plaque forming units) to $10^8$ pfus by serial dilution. A series of experiments are done to measure the tumor volume until regression or a maximum of 1 cm$^3$. Another series of experiment are performed to measure the intratumoral amount of virus in a time course. This amount is measured by resecting the tumors and staining sections with anti-hexon antibody (Chemicon) and b y extracting the virus from the tumors and measuring the viable virus in a plaque assay. In DU145 tumors, no therapeutic effect is observed with the PSA-controlled viruses. In LNCaP tumors, smaller tumors or complete tumor regressions is observed, and more intratumoral virus in tumors treated with the PSA-controlled replicative viruses is observed when compared to the non-replicative and vehicle control treated tumors. Smaller tumors or more frequent complete regressions are observed, likely due to higher amounts of intratumoral virus with the RGD-modified vector. These results demonstrate that the tumor-specific regulation of adenoviral genes, such as E4, allows replication in vivo in permissive tumors and also demonstrates the therapeutic advantage of the RGD modification for a replicative adenovirus.

EXAMPLE 13

Local-regional and Disseminated Models

A murine model for ovarian cancer and liver metastases of colon cancer has been developed. These models have been useful in demonstrating the utility of the RGD modification for non-replicative adenoviral vectors, and therefore, are used herein in the context of replicative adenoviruses containing tumor-specific promoters. The ovarian cancer model is a local-regional model that uses the human ovarian cancer cell line, SKOV3.ip1. As these cells express SLPI, this model is useful to evaluate viruses in which the E4 or E2 gene is regulated by the SLPI promoter. This cell line has been serially passaged in SCID mice and selected for its ability to grow aggressively in the peritoneum [62]. Female SCID mice receive an i.p. injection of $2 \times 10^7$ cells in 0.5 ml of serum-free medium. Five days after injection, tumors start to form at the peritoneum surface and the progression of the disease mimics the human disease. One week after injection, the viruses (RGD-modified or the unmodified control) will be injected i.p. in a volume of 100 µl. The therapeutic viruses are also intravenously injected. Virus dosages range from $10^4$ pfus to $10^8$ pfus. The therapeutic effect is measured by surviving cells. The amount of replicating virus is measured in peritoneal lavages in time course experiments.

The model of colon cancer liver metastases uses LS174T human colon cancer cells and allows for expression of genes under the CEA promoter. In a surgical operation, cells ($5 \times 10^8$) are injected along the long axis of the spleen. Five minutes after the injection, the splenic vessels are tied off and the spleen is cut and removed. After the abdominal wall and skin are sutured, extensive liver metastases form in 7–10 days. Tail vein injection of RGD-modified and unmodified replicative adenoviruses to demonstrate systemic treatment using this model. Liver metastases are counted in a time course experiment after virus injection.

These experiments provide in vivo data demonstrating selective replication and oncolytic potency of replicative vectors with restricted replication and enhanced infectivity. The RGD modification in the fiber of replicative adenoviruses, along with tumor-selective expression of E4 or E2 in addition to E1, increases the virus' propagation efficacy and ultimately its therapeutic efficacy.

EXAMPLE 14

Vertebrate Animals

Mice containing human tumors are used to evaluate the therapeutic potential of adenoviruses with enhanced infectivity and tumor-selective replication. Three types of models are used: subcutaneous engrafted cell lines (prostate LNCaP and DU145), diffuse intraperitoneal engraftments (ovarian SKOV3-ip1), and liver metastases (colorectal carcinoma cell line LS174T). Adult (6–8 week old) athymic nu/nu mice are used in the subcutaneous and metastatic models and SCID mice are used in the intraperitoneal model. Except for the prostate cell lines, female mice are used. Treatments include the RGD-modified, non-modified and vehicle control in a single injection for each dose. Intratumoral, intraperitoneal or intravenous administration of the viruses (according to the model used) is performed with unsedated mice using gentle physical restraint. All mice are euthanized at the conclusion of all experiments by $CO_2$ vapor sedation followed by Phenobarbital overdose.

The following references were cited herein:
1. Anderson, W. F., Nature, 1998. 392(6679 Suppl): p. 25–30.
2. Roth, et al., J Natl Cancer Inst, 1997. 89(1): p. 21–39.
3. Urban, J. L., et al., J Immunol, 1986. 137(9): p. 3036–41.
4. Paillard, F., Hum Gene Ther, 1998. 9(17): p. 2457–8.
5. Carbone, F. R., et al., Immunol Today, 1998. 19(8): p. 368–73.
6. Schreiber, H., Tumor Immunology, in Fundamental Immunology, W. E. Paul, Editor. 1999, Lippincott-Raven Publishers: Philadelphia. p. 1237–1270.
7. Cook, D. R., et al., Cancer Biother, 1994. 9(2): p. 131–41.
8. Moolten, F. L., Cancer Gene Ther, 1994. 1(4): p. 279–87.
9. Alemany, R., et al., Cancer Gene Ther, 1996. 3(5): p. 296–301.
10. Gomez-Manzano, C., et al., Cancer Res, 1996. 56(4): p. 694–9.
11. Rasmussen, et al., Pharmacol Ther, 1997. 75(1): p. 69–75.
12. Tanaka, T., et al., Cancer Res, 1998. 58(15): p. 3362–9.

13. Zhang, et al., Cancer Metastasis Rev, 1996. 15(3): p. 385–401.
14. Yeh, P. & M. Perricaudet, FASEB J, 1997. 11(8): p. 615–23.
15. Mittereder, N., et al., J Virol, 1996. 70(11): p. 7498–509.
16. Fallaux, F. J., et al., Hum Gene Ther, 1998. 9(13): p. 1909–17.
17. Smith, C. A., et al., J Virol, 1996. 70(10): p. 6733–40.
18. Deng, Y., et al., J Immunol, 1997. 158(4): p. 1507–15.
19. Worgall, S., et al., Hum Gene Ther, 1997. 8(1): p. 37–44.
20. Goldman, C. K., et al., Cancer Res, 1997. 57(8): p. 1447–51.
21. Miller, C. R., et al., Cancer Res, 1998. 58(24): p. 5738–48.
22. Hemmi, S., et al., Hum Gene Ther, 1998. 9(16): p. 2363–73.
23. Dmitriev, I., et al., J Virol, 1998. 72(12): p. 9706–13.
24. Krasnykh, V., et al., J Virol, 1998. 72(3): p. 1844–52.
25. Yoshida, Y., et al., Hum Gene Ther, 1998. 9(17): p. 2503–15.
26. Wickham, T. J., et al., J Virol, 1997. 71(11): p. 8221–9.
27. Miller, N. & J. Whelan, Hum Gene Ther, 1997. 8(7): p. 803–15.
28. Russell, S. J., Semin Cancer Biol, 1994. 5(6): p. 437–43.
29. Sinkovics, et al., Intervirology, 1993. 36(4): p. 193–214.
30. Kirn, & McCormick, Mol Med Today, 1996. 2(12): p. 519–27.
31. Goldsmith, K. T., et al., Hum Gene Ther, 1994. 5(11): p. 1341–8.
32. Kirn, D., et al., Nat Med, 1998. 4(12): p. 1341–2.
33. Rodriguez, R., et al., Cancer Res, 1997. 57(13): p. 2559–63.
34. Schuepbach, J. & C. Sauter, Cancer, 1981. 48(6): p. 1363–7.
35. Goodrum, F. D. & D. A. Ornelles, J Virol, 1998. 72(12): p. 9479–90.
36. Rothmann, T., et al., J Virol, 1998. 72(12): p. 9470–8.
37. Dobner, T., et al., Science, 1996. 272(5267): p. 1470–3.
38. Hall, A. R., et al., Nat Med, 1998. 4(9): p. 1068–72.
39. Shi, Q., et al., Hum Gene Ther, 1997. 8(4): p. 403–10.
40. Nelson, J. E. & M. A. Kay, J Virol, 1997. 71(11): p. 8902–7.
41. Bergelson, J. M., et al., Science, 1997. 275(5304): p. 1320–3.
42. Xia, et al., Curr Top Microbiol Immunol, 1995. 199 (1): p. 39–46.
43. Goldsmith, K. T., et al., Virology, 1998. 248(2): p. 406–19.
44. Scaria, A., et al., Gene Ther, 1995. 2(4): p. 295–8.
45. Arap, W., et al., Science, 1998. 279(5349): p. 377–80.
46. Pasqualini, R., et al., Nat Biotechnol, 1997. 15(6): p. 542–6.
47. Chartier, C., et al., J Virol, 1996. 70(7): p. 4805–10.
48. Dion, L. D., et al., Cancer Gene Ther, 1996. 3(4): p. 230–7.
49. Dion, L. D., et al., Gene Ther, 1996. 3(11): p. 1021–5.
50. Spergel, et al., Proc Natl Acad Sci USA, 1991. 88(15): p. 6472–6.
51. Takenawa, et al., J Natl Cancer Inst, 1991. 83(22): p. 1668–72.
52. Eustace, D., et al., Gynecol Oncol, 1993. 50(1): p. 15–9.
53. Kong, B., et al., Gynecol Oncol, 1996. 63(1): p. 78–84.
54. Murray, E. J., et al., Mol Cell Biol, 1991. 11(11): p. 5534–40.
55. Moran, E., Faseb J, 1993. 7(10): p. 880–5.
56. Gotoh, A., et al., J Urol, 1998. 160(1): p. 220–9.
57. Bangma, C. H., et al., Jama, 1996. 275(11): p. 837–8.
58. Amalfitano et al., Proc Natl Acad Sci USA, 1996 93(8): 3352–6.
59. Ferrin, L. J., Genet Eng (N Y), 1995. 17: p. 21–30.
60. Raben, D., et al., Gene Ther, 1996. 3(7): p. 567–80.
61. Garver R I, Jr., et al., Gene Ther, 1994. 1(1): p. 46–50.
62. Yu, D., et al., Cancer Res, 1993. 53(4): p. 891–8.
63. Hardy, S., et al., J. Virol., 1997. 71: p. 1842–1849.
64. Kasono, K., et al., Clin. Cancer Res., 1999. 5: p. 2571–2579.
65. Fueyo, J., et al., Oncogene, 1999. 19: p. 1–11.
66. Zheng, D. Q., et al., Cancer Res., 1999. 59: p. 1655–1664.
67. Rokhlin, O. W., et al., Prostate, 1995. 26: p. 205–212.
68. Alemany, R., et al., Exp. Cell. Res., 1999. 252: p. 1–12.
69. Todo, T., et al., Hum. Gene Ther., 1999. 10: p. 2741–2755.
70. Heise, C. C., et al., Cancer Gene Ther., 1999. 6: p. 499–504.
71. Shinoura, N., et al., Cancer Res., 1999. 59: p. 3411–3406.
72. Koivunen, E., et al., J. Nucl. Med., 1999. 40: p. 883–888.
73. Roelvink, P. W., et al., Science, 1999. 286: p. 1568–1571.
74. Yu, D. C., et al., Cancer Res., 1999. 59: p. 1498–1504.
75. Bischoff, J. R., et al., Science, 1996. 274: p. 373–376.
76. Wildner, O., et al., Gene Ther., 1999. 6: p. 57–62.
77. Wildner, O., et al., Cancer Res., 1999. 59: p. 410–413.
78. Freytag, S. O., et al., Hum. Gene Ther., 1998. 9: p. 1323–1333.
79. Heise, C., et al., Nat. Med., 1997. 3: p. 639–645.
80. Yang, Y., et al., Nat. Med., 1995. 1: p. 890–893.
81. Kremer, E. J., et al., J. Virol., 2000. 74: p. 505–512.
82. Hofmann, C., et al., J. Virol., 1999. 73: p. 6930–6936.
83. Fechner, H., et al., Gene Ther., 1999. 6: p. 1520–1535.
84. O'Riordan, C., et al., Hum. Gene Ther. 1999. 10: p. 1349–1358.
85. Blackwell et al., Arch. Otolaryngol. Head Neck Surg. 1999. 125: P. 856–863.
86. Krasnykh et al., J. Virol., 1996. 70: p. 6839–6846.
87. Stevenson et al., J. Virol., 1995. 69: p. 2850–2857.
88. Von Seggern et al., J. Virol., 2000. 74: p. 354–362.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

SEQUENCE LISTING

<160> NUMBER OF SEQ ID NOS: 5

<210> SEQ ID NO 1
<211> LENGTH: 9
<212> TYPE: PRT
<213> ORGANISM: artificial sequence
<220> FEATURE:
<223> OTHER INFORMATION: Amino acid sequence of an RGD peptide which
      binds with high affinity to some integrins the encoding sequence
      of which is introduced into the HI loop of the fiber knob

<400> SEQUENCE: 1

Cys Asp Cys Arg Gly Asp Cys Phe Cys
                5

<210> SEQ ID NO 2
<211> LENGTH: 20
<212> TYPE: DNA
<213> ORGANISM: artificial sequence
<220> FEATURE:
<223> OTHER INFORMATION: FiberUp primer used to verify the presence of
      the RGD motif in the modified fiber.

<400> SEQUENCE: 2
caaacgctgt tggatttatg                                              20

<210> SEQ ID NO 3
<211> LENGTH: 21
<212> TYPE: DNA
<213> ORGANISM: artificial sequence
<220> FEATURE:
<223> OTHER INFORMATION: FiberDown primer used to verify the presence of
      the RGD motif in the modified fiber.

<400> SEQUENCE: 3
gtgtaagagg atgtggcaaa t                                            21

<210> SEQ ID NO 4
<211> LENGTH: 20
<212> TYPE: DNA
<213> ORGANISM: artificial sequence
<220> FEATURE:
<223> OTHER INFORMATION: E1a-1 primer used to verify the (24 base pair
      deletion from the E1A gene in the modified fiber.

<400> SEQUENCE: 4
attaccgaag aaatggccgc                                              20

<210> SEQ ID NO 5
<211> LENGTH: 19
<212> TYPE: DNA
<213> ORGANISM: artificial sequence
<220> FEATURE:
<223> OTHER INFORMATION: E1a-2 primer used to verify the (24 base pair
      deletion from the E1A gene in the modified fiber.

<400> SEQUENCE: 5
ccatttaaca cgccatgca                                               19

---

What is claimed is:

1. A method for reducing tumor burden in a subject in need thereof comprising administering to the subject in need thereof a therapeutically effective amount of a modified conditionally replicative adenovirus; said modified conditionally replicative adenovirus having greater infectivity in tumor cells than wild-type adenovirus, and hence is modified, by:
the modified conditionally replicative adenovirus having a modified fiber protein containing a ligand, by the conditionally replicative adenovirus containing and expressing a nucleotide sequence encoding the ligand, and wherein the ligand comprises Arg-Gly-Asp in the HI loop of the fiber; or the modified conditionally repticative adenovirus containing a fiber knob domain from a different subtype of adenovirus;

whereby the ligand or fiber knob domain provides a pathway to cell binding by the modified conditionally replicative adenovirus other than the coxsackie-adenovirus receptor, and thereby enhances infectivity of the conditionally replicative adenovirus in tumor cells over that of wild-type adenovirus, and wherein the modified conditionally replicative adenovirus contains a deletion of nucleotide sequences encoding the E1b-55K protein, or the RB binding site of E1a, such that the replicating adenovirus infects the tumor cells, and thereby reduces tumor burden in the subject.

2. The method of claim 1 wherein the modified conditionally replicative adenovirus has the modified fiber protein containing the ligand comprising Arg-Gly-Asp in the HI loop.

3. The method of claim 1 wherein the modified conditionally replicative adenovirus has the fiber domain from a different subtype of adenovirus.

4. The method of claim 1 wherein the modified conditionally replicative adenovirus contains a deletion of nucleotide sequences encoding the RB binding site of E1a.

5. The method of claim 1 wherein the modified conditionally replicative contains a deletion of nucleotide sequences encoding the E1-55K protein.

6. The method of claim 2 wherein the modified conditionally replicative adenovirus contains a deletion of nucleotide sequences encoding the RB binding site of E1a.

7. The method of claim 2 wherein the modified conditionally replicative contains a deletion of nucleotide sequences encoding the E1b-55K protein.

8. The method of claim 3 wherein the modified conditionally replicative adenovirus contains a deletion of nucleotide sequences encoding the RB binding site of E1a.

9. The method of claim 3 wherein the modified conditionally replicative adenovirus is a subtype 5 having the fiber domain from an adcnovirus subtype 3.

10. The method of claim 8 wherein the modified conditionally replicative adenovirus is a subtype 5 having the fiber domain from an adenovirus subtype 3.

11. The method of claim 1 wherein the modified conditionally replicative adenovirus provides a pathway to cell binding by the adenovirus other than the coxsackie-adenovirus receptor by containing the ligand, and the ligand has the sequence of SEQ ID NO:1.

12. The method of claim 1 wherein the modified conditionally replicative adenovirus is further modified by containing and expressing an exogenous nucleotide sequence encoding a therapeutic polypeptide.

* * * * *